US008680217B2

(12) United States Patent
Hefner, Jr. et al.

(10) Patent No.: US 8,680,217 B2
(45) Date of Patent: Mar. 25, 2014

(54) POLYCYCLOPENTADIENE COMPOUNDS

(75) Inventors: Robert E. Hefner, Jr., Rosharon, TX (US); Michael J. Mullins, Houston, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/643,328

(22) PCT Filed: Apr. 21, 2011

(86) PCT No.: PCT/US2011/000705
§ 371 (c)(1),
(2), (4) Date: Oct. 25, 2012

(87) PCT Pub. No.: WO2011/136843
PCT Pub. Date: Nov. 3, 2011

(65) Prior Publication Data
US 2013/0046067 A1    Feb. 21, 2013

Related U.S. Application Data

(60) Provisional application No. 61/329,334, filed on Apr. 29, 2010.

(51) Int. Cl.
*C08G 8/04* (2006.01)
*C08G 8/28* (2006.01)
(52) U.S. Cl.
USPC ............................................. 525/502
(58) Field of Classification Search
USPC ............................................. 525/502
See application file for complete search history.

(56) References Cited

U.S. PATENT DOCUMENTS

| | | | |
|---|---|---|---|
| 3,298,998 A | 1/1967 | McConnell et al. | |
| 3,419,642 A | 12/1968 | McGary, Jr. et al. | |
| 4,546,129 A | 10/1985 | Hefner, Jr. | |
| 4,623,701 A | 11/1986 | Massingill | |
| 5,138,101 A * | 8/1992 | Devon | 568/492 |
| 5,736,620 A | 4/1998 | Earls et al. | |
| 6,307,108 B1 | 10/2001 | Argyropoulos et al. | |
| 7,321,068 B2 | 1/2008 | Papp et al. | |
| 2011/0009559 A1* | 1/2011 | Mullins et al. | 524/589 |
| 2011/0009560 A1* | 1/2011 | Hefner et al. | 524/590 |
| 2011/0098380 A1* | 4/2011 | Hearn et al. | 523/400 |

FOREIGN PATENT DOCUMENTS

| | | |
|---|---|---|
| EP | 0556429 | 2/1992 |
| GB | 1009019 | 11/1965 |
| WO | 2005118604 | 12/2005 |
| WO | 2009114383 | 9/2009 |
| WO | WO 2009114383 A1 * | 9/2009 |
| WO | WO 2009114466 A1 * | 9/2009 |

OTHER PUBLICATIONS

International Search Report and Written Opinion from related PCT application PCT/US2011/000705 dated Jul. 14, 2011, 12 pages.
International Preliminary Report on Patentability from related PCT application PCT/US2011/000705 dated Jun. 2, 2012, 20 pages.
H.E. Lee and K. Neville, "Handbook of Epoxy Resins", McGraw-Hill, New York, 1967, chapter 2, pp. 2-1 through 2-33.
Zahir, et al. "Studies in Photodimerization of the Diglycidyl Ether of 4,4'-Dihydroxychalcone", Journal of Applied Polymer Science, vol. 23, 1972, 1355-1372.
L.R. Whittington, Whittington's Dictionary of Plastics, definition of "thermosetting plastics", 1978, p. 314.
Longoni, et al. "Hydroformylation and hydrocaronylation of dicyclopentadiene with cobalt-rhodium catalytic systems promoted by truphenylphosphine: Synthesis of monoformyltricyclodecenes, diformyltricyclodecanes and di (tricyclodecenyl) ketones", Molecular Catalysis 68, (1991), 7-21.
Kirk-Othmer, Encyclopedia of Chemical Technology, 5th ed., vol. 10, (2010), 347-470.
Kirk-Othmer, Encyclopedia of Chemical Technology, 5th ed., vol. 8, (2010), pp. 219-235.
Byrne, et al. "Magnesium-Oppenauer Oxidation of Alcohols to Aldehydes and Ketones", Tetrahedron Letters, vol. 28, No. 7, 1987, pp. 769-772.
Hirao, et al. "Versatile Synthesis of ab-acetylenic ketones by oxidative nucleophilic addition of vanadium acetylides" Tetrahedron Letters, No. 27, No. 8, 1986, pp. 933 and 934.
Journal of the American Chemical Society, No. 107, 1985, 7179-7181.
Adlington, et al. "Azo Anions in Synthesis t-Butylhydrazones as Acyl-anion Equivalents", Journal of the Chemical Society: Chemical Communications, 1983, 1040-1041.
Koph "Phenolic Resins", Kirk-Othmer, Encyclopedia of Chemical Technology, vol. 0, 2010, pp. 1-53.
Jay, "Direct Titration of Epoxy Compounds and Aziridines", Analytical Chemistry, vol. 36, No. 3, 1964, 667-668.

* cited by examiner

*Primary Examiner* — Mike M Dollinger
(74) *Attorney, Agent, or Firm* — Brooks, Cameron & Huebsch, PLLC

(57) ABSTRACT

The present disclosure provides for polycyclopentadiene compounds that useful as an epoxide resin and/or as an adduct for a curable composition.

16 Claims, No Drawings

POLYCYCLOPENTADIENE COMPOUNDS

This application is a National Stage application under 35 U.S.C. 371 of PCT/US2011/000705, filed on Apr. 21, 2011 and published as WO2011/136843 A1 on Nov. 3, 2011, which claims the benefit of U.S. Provisional Application Ser. No. 61/329,334 filed Apr. 29, 2010, the entire contents of which are incorporated herein by reference in its entirety.

FIELD OF DISCLOSURE

This disclosure relates to polycyclopentadiene compounds, and in particular to resins and adducts of the polycyclopentadiene compounds and their use in curable compositions.

BACKGROUND

Phenolic resins are synthetic materials that vary greatly in molecular structure. This variety allows for a multitude of applications for these resins. One example of a phenolic resin is polycyclopentadiene diphenol, which is discussed in U.S. Pat. Nos. 3,419,624 and 4,546,129. Polycyclopentadiene diphenol may be used as a curing agent and/or to prepare the corresponding epoxy, cyanate and/or allyl thermosettable resin. These curing agents and/or resins can provide enhanced physical and/or mechanical properties to a cured composition due to the presence of the dicyclopentadienyl moiety and/or the functional group (e.g., the diphenol moiety). For example, cured compositions formed from such resins can have both a high glass transition temperature (Tg) and a relatively low water uptake.

To achieve these properties, however, would require the resin to have a high functionality (i.e., chemical groups available for crosslinking). As the functionality increases in these resins, so does their molecular weight. As the molecular weight increases, so does the melt viscosity of the resin. Having a high melt viscosity can lead to difficulties in using such resins.

SUMMARY

The present disclosure provides for polycyclopentadiene compounds that are useful as an epoxide resin and/or as an adduct for a curable composition. The use of the polycyclopentadiene compounds of the present disclosure as either curing agents and/or as an adduct in a curable composition can provide the resulting cured composition with an enhanced glass transition temperature. Additionally, it is expected that the polycyclopentadiene compounds of the present disclosure will also provide improvements in both moisture resistance and corrosion resistance, as well as enhanced electrical properties, of the cured composition, especially dissipation factor.

For the various embodiments, the polycyclopentadiene compound of the present disclosure has a structure of Formula I:

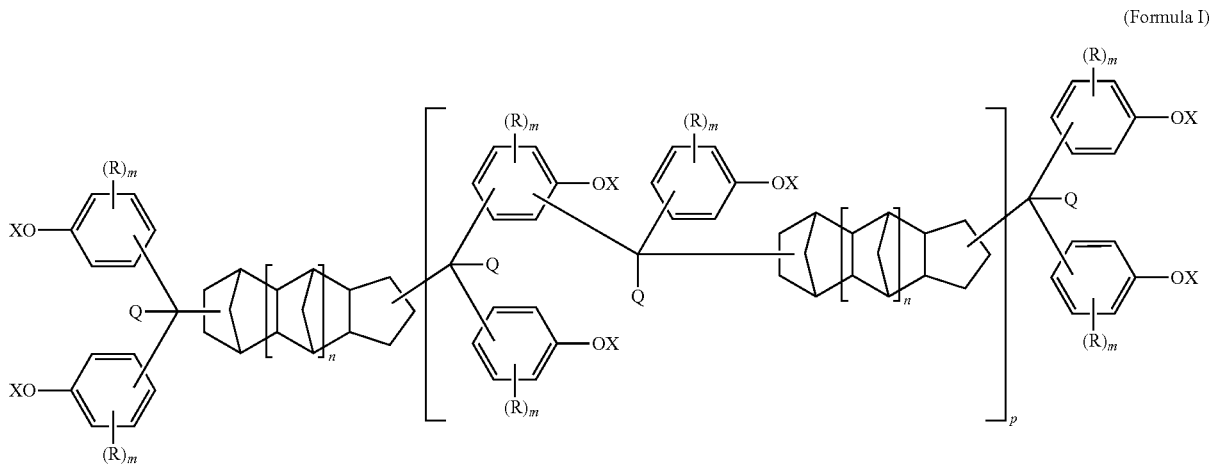

(Formula I)

in which X is a structure of Formula II:

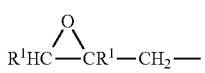

(Formula II)

where each $R^1$ is independently hydrogen or a methyl group, n has an average value from zero to 20; each m independently has a value of zero to 3; each p has a value of zero to 20; each R is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to about 6 carbon atoms, and each Q is independently hydrogen or an alkyl group containing 1 to about 6 carbon atoms. Embodiments of the present disclosure also include a polycyclopentadiene structure of Formula III:

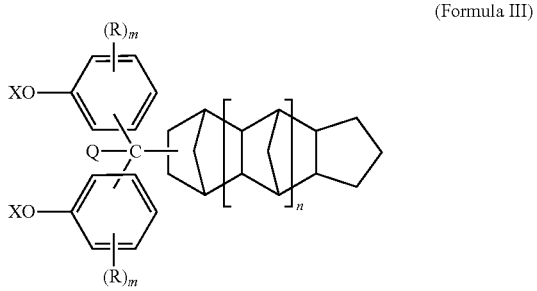
(Formula III)

in which X is a structure of Formula II:

(Formula II)

where each $R^1$ is independently hydrogen or a methyl group, n has an average value from zero to about 20; each m independently has a value of zero to 3; each R is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to about 6 carbon atoms, and each Q is independently hydrogen, an alkyl group containing 1 to about 6 carbon atoms, or a structure of Formula IV

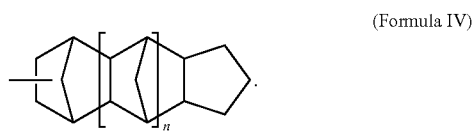
(Formula IV)

Embodiments of the present disclosure also include an adduct prepared from the polycyclopentadiene compound of Formula I and/or Formula III and a hydrogen containing compound that includes one or more reactive hydrogen atoms reactive with epoxide groups of the polycyclopentadiene compound. For the various embodiments, the present disclosure also includes a curable composition that includes the polycyclopentadiene compound of Formula I and/or Formula III and a hardener.

In additional embodiments, the curable composition of the present disclosure can include an adduct formed with the polycyclopentadiene compound of Formula I and/or Formula III and a resin. For the various embodiments, the resin can include the polycyclopentadiene compound of Formula I and/or Formula III. In additional embodiments, the resin can be an epoxy resin other than and/or in addition to the polycyclopentadiene compound of Formula I and/or Formula III. Embodiments of the present disclosure can also include oligomers formed from the polycyclopentadiene compounds of Formula I and/or Formula III. Embodiments of the present disclosure can also include a cured or partially cured composition resulting from curing the curable composition of the present disclosure.

The above summary of the present disclosure is not intended to describe each disclosed embodiment or every implementation of the present disclosure. The description that follows more particularly exemplifies illustrative embodiments. In several places throughout this disclosure, guidance is provided through lists of examples, which examples can be used in various combinations. In each instance, the recited list serves only as a representative group and should not be interpreted as an exclusive list.

DETAILED DESCRIPTION

The present disclosure provides for polycyclopentadiene compounds that may be useful as an epoxide resin and/or as an adduct in a curable composition. The polycyclopentadiene compounds of the present disclosure may provide high level functionality when used in a curable composition. Curable compositions formed with the polycyclopentadiene compounds and/or the adducts of the present disclosure may also provide for cured compositions that have an enhanced glass transition temperature (Tg). Additionally, it is expected that the polycyclopentadiene compounds and/or adducts of the present disclosure will also provide improvements in both moisture resistance and corrosion resistance, as well as enhanced electrical properties, of the cured composition, especially dissipation factor.

As used herein, "a," "an," "the," "at least one," and "one or more" are used interchangeably. The terms "includes" and "comprises" and variations thereof do not have a limiting meaning where these terms appear in the description and claims.

The term "and/or" means one, one or more, or all of the listed items.

The recitations of numerical ranges by endpoints include all numbers subsumed within that range (e.g., 1 to 5 includes 1, 1.5, 2, 2.75, 3, 3.80, 4, 5, etc.).

Unless otherwise stated, a reference to a material, a compound, or a component includes the material, compound, or component by itself, as well as in combination with other materials, compounds, or components, such as mixtures and combinations of compounds.

As used herein, the term "adduct" means a product of a direct addition of two or more distinct molecules, resulting in a single reaction product. The resultant reaction product or adduct is considered a distinct molecular species from the reactants.

The term "thermoset" as used herein refers to a polymer that can solidify or "set" irreversibly when heated.

The terms "curable," "cured," "thermosettable" and "thermoset" are used synonymously throughout and mean that the composition is capable of being subjected to conditions which will render the composition to a cured or thermoset state or condition. The term "cured" or "thermoset" is defined by L. R. Whittington in *Whittington's Dictionary of Plastics* (1968) on page 239 as follows: "Resin or plastics compounds which in their final state as finished articles are substantially infusible and insoluble. Thermosetting resins are often liquid at some stage in their manufacture or processing, which are cured by heat, catalysis, or some other chemical means. After being fully cured, thermosets cannot be resoftened by heat. Some plastics which are normally thermoplastic can be made thermosetting by means of crosslinking with other materials."

The term "B-stage" as used herein refers to a thermoset resin that has been thermally reacted beyond the A-stage so that the product has full to partial solubility in a solvent such as an alcohol or a ketone.

The term "alkyl group" means a saturated linear or branched monovalent hydrocarbon group including, for example, methyl, ethyl, n-propyl, isopropyl, t-butyl, pentyl, hexyl, and the like.

The term "alkoxy group" refers to groups where at least one hydrocarbon alkyl group is bonded to an oxygen. For example, a group represented by the formula —O—R or —O—R—O—R is an alkoxy group, where R is the hydrocarbon alkyl group.

The term "alkenyl group" means an unsaturated, linear or branched monovalent hydrocarbon group with one or more olefinically unsaturated groups (i.e., carbon-carbon double bonds), such as a vinyl group.

The term "alkenyloxy group" refers to groups where at least one hydrocarbon alkenyl group is bonded to an oxygen.

In the following detailed description, the specific embodiments of the present disclosure are described in connection with its preferred embodiments. However, to the extent that the following description is specific to a particular embodiment or a particular use of the present techniques, it is intended to be illustrative only and merely provides a concise description of the exemplary embodiments. Accordingly, the present disclosure is not limited to the specific embodiments described herein, but rather; the disclosure includes all alternatives, modifications, and equivalents falling within the true scope of the appended claims.

For the various embodiments, the polycyclopentadiene compound of the present disclosure has a structure of Formula I:

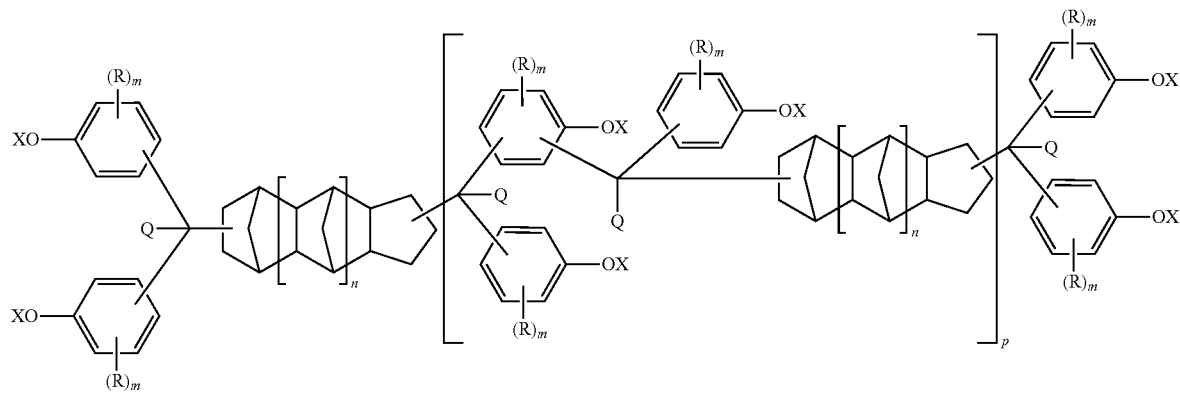

(Formula I)

in which X is a structure of Formula II:

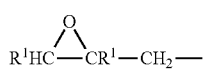

(Formula II)

where each $R^1$ is independently hydrogen or a methyl group, n has an average value from zero to 20; each m independently has a value of zero to 3; each p has a value of zero to 20; each R is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to about 6 carbon atoms, and each Q is independently hydrogen or an alkyl group containing 1 to about 6 carbon atoms.

For the various embodiments, the polycyclopentadiene compound of the present disclosure is also represented by a structure of Formula III:

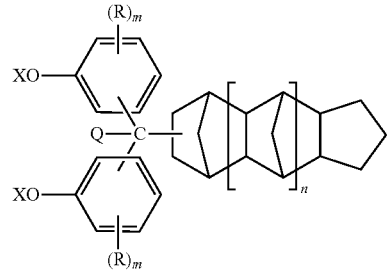

(Formula III)

in which X, n, m, and R are as provided herein, and each Q is independently hydrogen, an alkyl group containing 1 to about 6 carbon atoms, or a structure of Formula IV

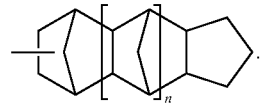

(Formula IV)

For the various embodiments, the halogen of the polycyclopentadiene compounds is preferably selected from the group of fluorine, chlorine, bromine and combinations thereof. The various embodiments also provide that n can have an average value from zero to about 8. Preferably, p has a value from zero to 5, and more preferably p has a value from zero to 1. For the various embodiments, the alkyl group and/or the alkoxy group can preferably contain 1 to about 4 carbon atoms, more preferably 1 to about 2 carbon atoms. For the various embodiments, the alkenyl group and the alkenyloxy group preferably contain 1 to about 3 carbon atoms. For the various embodiments, when Q is an alkyl group it preferably contains 1 to about 4 carbon atoms, and more preferably it contains 1 to about 2 carbon atoms. Preferably, the alkyl group and/or the alkoxy group are substituted with a halogen atom. For the various embodiments, the halogen atom in either of the alkyl group and/or the alkoxy group are each independently selected from the group consisting of chlorine, bromine and combinations thereof.

For the various embodiments, when m has a value other than zero, the carbon bonded to Q

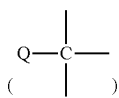

is preferably in the ortho and/or para position relative to the —OX group. It is appreciated that mixtures of compounds having the carbon bonded to the Q in both the ortho and the para position relative to the —OX group are possible. It is also possible to have the carbon bonded to Q

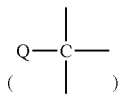

in the meta position relative to the —OX group.

Preparation of Polycyclopentadiene Polyphenols

For the various embodiments, polycyclopentadiene polyphenols can be used in preparing the polycyclopentadiene compounds of the present disclosure. For the various embodiments, polycyclopentadiene polyphenols can be produced from polycyclopentadiene dialdehydes and/or polycyclopentadiene diketones. For the various embodiments, polycyclopentadiene dialdehydes can be produced via hydroformylation of polycyclopentadiene, in particular, dicyclopentadiene, using syngas, a phosphine ligand, and a transition metal (from Groups 3 through 10) catalyst using a method such as described by G. Longoni, et al, J. of Molecular Catalysis 68, 7-21 (1991) or more generally in Kirk-Othmer, ENCYCLOPEDIA OF CHEMICAL TECHNOLOGY, Fifth Edition, Vol. 10, pp. 347-470 (2010). There are many variations in this process, including a method (U.S. Pat. No. 6,307,108 B1) that uses mixed polar/nonpolar solvents to ease the problem of catalyst recycle and product separation. The resulting polycyclopentadiene dialdehydes can then be condensed with phenols to form polycyclopentadiene polyphenols. Polycyclopentadiene can be prepared by heating cyclopentadiene to temperatures above 100° C. as disclosed by Kirk-Othmer, ENCYCLOPEDIA OF CHEMICAL TECHNOLOGY, Fifth Edition, Vol. 8, p. 223 (2010). All of the aforementioned references are incorporated herein in their entirety by reference.

For the various embodiments, the hydroformylation can occur at a pressure of 1 to 250 atmospheres (atm) and a temperature of 20° C. to 250° C. For the various embodiments, the syngas can contain varying amounts of carbon monoxide (CO), hydrogen ($H_2$) and, possibly, inert gases. The reaction also can be conducted using a rhodium catalyst without a ligand as disclosed in U.S. Pat. No. 7,321,068, albeit at high syngas pressures of 200-350 atm. Examples of suitable ligands include carbon monoxide and organophosphine ligands having the general formula $PR^1R^2R^3$ where each $R^1$, $R^2$, and $R^3$ is a substituted or unsubstituted alkyl, an aryl, an aralkyl, an alkaryl, a halide, or a combination thereof. A specific example includes, but is not limited to, n-butyldiphenylphosphine. An example of a suitable catalyst includes, but is not limited to, $Rh(CO)_2$(acetylacetonate).

During the hydroformylation minor amounts, typically 5-25 weight (wt.) percent (%) or less of the total reaction products, of partially or totally saturated polycyclopentadiene monoaldehydes may also be produced along with the polycyclopentadiene dialdehydes. An example of these saturated polycyclopentadiene monoaldehydes with saturated cyclopentane ring is represented by the following Formula V, where n is as described herein:

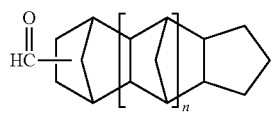

(Formula V)

The polycyclopentadiene monoaldehydes can be partially or totally separated from the polycyclopentadiene dialdehydes. For example, a distillation process could be used to separate the polycyclopentadiene monoaldehydes from the polycyclopentadiene dialdehydes.

In an additional embodiment, various weight percents of the polycyclopentadiene monoaldehydes with saturated cyclopentane ring could also be mixed with the polycyclopentadiene dialdehydes. Using mixtures of the polycyclopentadiene monoaldehydes and the polycyclopentadiene dialdehydes may allow for control of a level of functionality in the resulting curable composition. For example, whereas novolac chemistry can be used to form the polycyclopentadiene polyphenols from the polycyclopentadiene dialdehydes, novolac chemistry can also be used to form polycyclopentadiene diphenols from the polycyclopentadiene monoaldehydes. An example of the polycyclopentadiene diphenols with saturated cyclopentane ring is represented by the following Formula VI:

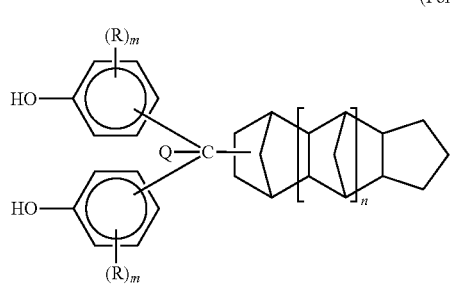

(Formula VI)

where n, m, R and Q are as described herein. Oligomers may also be present in the polycyclopentadiene diphenols. Thus, mixtures of polycyclopentadiene diphenols and polyphenols may be produced as an additional embodiment of the present disclosure. As such, it is appreciated that the discussion pertaining to the use and reactions involving polycyclopentadiene polyphenols applies also to polycyclopentadiene diphenols and mixtures of the polycyclopentadiene polyphenols and diphenols.

For the various embodiments, polycyclopentadiene diketones useful in the present disclosure can be produced through a multistep synthesis, for example the chemistry given in Tetrahedron Letters, 28, 769 (1987); Tetrahedron Letters, 27, 3033 (1986); Tetrahedron Letters, 27, 933 (1986); Journal of the American Chemical Society, 107, 7179 (1985); and Journal of the Chemical Society: Chemical Communications, 1040 (1983). All of the references mentioned herein are incorporated herein in their entirety by reference.

Hydroformylation can also produce small amounts of isomeric ketones as described by Longoni. These ketones can be the predominant products when the $H_2$/CO pressure is low (~1 atm). If these ketones are present in the product mix they can be condensed with phenol to form polyphenols of Formula VII, where n, m, and R are as described herein.

(Formula VII)

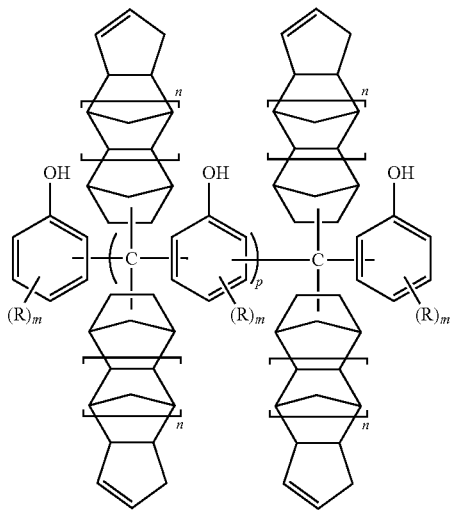

As provided herein, using mixtures of the polycyclopentadiene monoaldehydes, dialdehydes, and ketones may allow control over the level of functionality in a given curable composition. So, for example, the crosslink density for a curable composition of the present disclosure can be adjusted (e.g., decreased or increased) based on the relative amounts of the polycyclopentadiene polyphenols and the polycyclopentadiene diphenols used in the composition. Adjusting the level of functionality in this way may allow for the properties such as glass transition temperature (Tg) of the cured composition to tailor to desired levels and/or balance with other properties (e.g., toughness) of the cured composition.

Moreover, it may be possible to control the amount of dicyclopentadiene and/or polycyclopentadiene moieties in the polycyclopentadiene dialdehydes of the present disclosure. The dicyclopentadiene and/or polycyclopentadiene can be formed through Diels-Alder chemistry using cyclopentadiene where, as discussed herein, the average value for n of Formula I can be from zero to 20. So, for example, when the polycyclopentadiene moieties in the polycyclopentadiene dialdehydes of the present disclosure are oligomers they can have a distribution of n values that is on average from 2 to 5. For other embodiments, n can have a value of zero or 1. The ability to control the dicyclopentadiene and/or polycyclopentadiene moieties in the polycyclopentadiene dialdehydes may also allow for the ability to control and/or tailor a crosslink density of a curable composition while retaining or even increasing potential moisture resistance properties of the cured composition.

The resulting polycyclopentadiene dialdehydes along with any of the polycyclopentadiene monoaldehydes and ketones can then undergo a novolac reaction to form the polycyclopentadiene polyphenols and/or diphenols of the present disclosure. For the various embodiments, the novolac reaction involves the use of a phenol and an acid catalyst. For example, the polycyclopentadiene dialdehydes and molten phenol can be reacted at a temperature of 65° C. to 70° C. with stirring under a nitrogen atmosphere and in the presence of an acid catalyst. The resulting polycyclopentadiene dialdehydes, along with any of the polycyclopentadiene monoaldehydes, can then undergo a novolac reaction to form the polycyclopentadiene polyphenols and/or diphenols of the present disclosure. A general description of novolac preparation can be found in Kirk-Othmer, ENCYCLOPEDIA OF CHEMICAL TECHNOLOGY, 2010, Chapter "Phenolic Resins" by Peter W. Kopf.

For the various embodiments, polycyclopentadiene polyphenols of the present disclosure are prepared via a condensation reaction of a mole ratio of the polycyclopentadiene dialdehydes (and any polycyclopentadiene monoaldehydes) to phenol and/or substituted phenol, including, for example, o-cresol, m-cresol, p-cresol, 2,4-dimethylphenol, 2,6-dimethylphenol, 1-naphthol, and 2-naphthol, of 1:20 to 1:6, and preferably from 1:15 to 1:8; in the presence of an acid catalyst which is preferably from 0.1 to 2, and more preferably from 0.1 to 1 wt. % based on the amount of phenol or substituted phenol compound employed. Higher mole ratios than 1:20 of the phenol or substituted phenol may be employed, however doing so may require additional energy and thus expense to recover and recycle the excess phenol or substituted phenol.

Condensation reactions employing a large excess of the phenol and/or substituted phenol have been found to favor polycyclopentadiene polyphenols having a low polydispersity and weight average molecular weight. Likewise, as the amount of the phenol and/or substituted phenol is reduced, there can be an increase in oligomers of the polycyclopentadiene polyphenols, increasing the weight average molecular weight. Increased oligomer content favors higher hydroxyl functionality per molecule which may be highly beneficial for certain end uses, for example, increasing the Tg, but at the cost of higher viscosity. Thus, while very large excesses of phenol and/or substituted phenol may be used, the present disclosure in one embodiment employs the molar ratio provided above to produce products rich in polycyclopentadiene polyphenol, and low in oligomers.

For the various embodiments, condensation reactions to form the polycyclopentadiene polyphenols of the present disclosure may also optionally include the use of a solvent. For these embodiments, the solvent can be substantially inert to the reactants and reaction products formed. Examples of suitable solvents include, but are not limited to, toluene or xylene. The solvent may additionally serve as an agent for the azeotropic removal of water from the condensation reaction. With certain phenolic reactants with higher melt viscosities, use of one or more solvents may be beneficial for maintaining a suitable reaction medium.

Suitable acid catalysts include the protonic acids, such as hydrochloric acid, sulfuric acid, phosphoric acid; metal oxides, such as zinc oxide, aluminum oxide, magnesium oxide; organic acids, such as p-toluenesulfonic acid, oxalic acid, 3-mercapto-1-propane sulfonic acid and combinations thereof. For the various embodiments, the 3-mercapto-1-propane sulfonic acid is a preferred acid catalyst or co-catalyst. Surprisingly, it has been found that 3-mercapto-1-propane sulfonic acid is so highly active and selective in forming the polycyclopentadiene polyphenols that there is no need for an azeotropic removal of water from the reaction products. Rather, the water remains in the reactor, without quenching the novolac reaction.

Reaction temperatures and times vary, but can be from about 5 minutes to about 48 hours and reaction temperatures of from about 20° C. to about 175° C. may be employed. Preferably reaction temperatures and times can be from 15 minutes to 36 hours and reaction temperatures of from 30° C. to about 125° C. Most preferably reaction temperatures and times can be from 30 minutes to 24 hours and reaction temperatures of from 35° C. to about 75° C.

At the end of the reaction, the acidic catalyst can be removed by neutralization, for example and/or by washing or extraction with water. Likewise, at the end of the reaction, excess phenol can be removed from the novolac product, for example, by distillation or extraction.

For the various embodiments, the polycyclopentadiene polyphenols of the present disclosure can have a polydispersity index of 1 to 5, more preferably 1.2 to 2.5 and most preferably is 1.2 to 1.8. For example, the polydispersity index (the measure of distribution of molecular mass in a given sample) of the polycyclopentadiene polyphenols can be from 1.3 to 1.4. These types of results indicate that both the n values and the p values of each of the polycyclopentadiene polyphenols for the present disclosure are very uniform. This result is surprising, as novolac reactions often times produce products having a much larger polydispersity (e.g., from 2 to 5). Having a uniform chain length for the polycyclopentadiene polyphenols for the present disclosure allow for more desirable viscosity predictability in the viscosity of the curable compositions of the present disclosure.

The polydispersity values for certain of the polycyclopentadiene polyphenols of the present disclosure are indicative of an increase in the level of functionality without substantial increase in Mw. High functionality and the resultant high crosslink density can provide very desirable high Tg.

For the various embodiments, starting with the polycyclopentadiene dialdehydes allows for a high level of functionality to be achieved in the resulting polycyclopentadiene polyphenols without a large increase in the compound's Mw. This is not the case with previous attempts to form polyphenols with high levels of functionality. For example, embodiments of the present disclosure provide for functionalities of about 4 at hydroxyl equivalent weights as low as about 133 grams per hydroxyl equivalent. Embodiments of the present disclosure may also allow for a scalable progression in the level of functionality to be achieved without significant increases in the molecular weight and viscosity of the curable composition.

For the various embodiments, suitable polycyclopentadiene polyphenols that can be employed to prepare the compounds of the present disclosure include those represented by a compound of the following Formula VIII:

Preparation of Polycyclopentadiene Compounds

For the various embodiments, the polycyclopentadiene polyphenols, polycyclopentadiene diphenols and/or oligomers thereof can be formed into the polycyclopentadiene compounds of the present disclosure through a reaction with an epihalohydrin. For the various embodiments, the reaction can take place in the presence of a suitable basic acting substance, in the presence or absence of a catalyst and in the presence or absence of a solvent.

For the various embodiments, the reaction preferably takes place at a temperature of about 20° C. to about 120° C., more preferably at a temperature of about 30° C. to about 85° C., and most preferably at a temperature of about 40° C. to about 75° C. For the various embodiments, the reaction also preferably takes place at a pressure of about 30 mm Hg vacuum to about 690 KPa, more preferably at a pressure of about 30 mm Hg vacuum to about 345 KPa, and most preferably at a pressure of about 60 mm Hg vacuum to about 101 KPa (about 1 atmosphere). For the various embodiments, the reaction can take place at a time sufficient to complete the reaction, preferably from about 1 to about 120 hours, more preferably from about 3 to about 72 hours, and most preferably from about 4 to about 48 hours.

For the various embodiments, the reaction also uses from about 1.1:1 to 25:1, preferably from about 1.8:1 to about 10:1, and most preferably from about 2:1 to about 5:1 moles of epihalohydrin per phenolic hydroxy group. This initial reaction, unless the catalyst is an alkali metal or alkaline earth metal hydroxide employed in stoichiometric or greater quantities, produces a halohydrin intermediate which is then reacted with the basic acting substance to convert the vicinal halohydrin groups to epoxide groups. The resultant product is a glycidyl ether compound. Details concerning preparation of epoxy resins are given in U.S. Pat. No. 5,736,620; Handbook of Epoxy Resins by Lee and Neville, McGraw-Hill (1967); and Journal of Applied Polymer Science, volume 23, pages 1355-1372 (1972); and U.S. Pat. No. 4,623,701; all of which are incorporated herein by reference in their entirety.

For the various embodiments, suitable epihalohydrins that can be employed to prepare the compositions of the present disclosure include, for example, epichlorohydrin, epibromohydrin, epiiodohydrin, methylepichlorohydrin, methylepi-

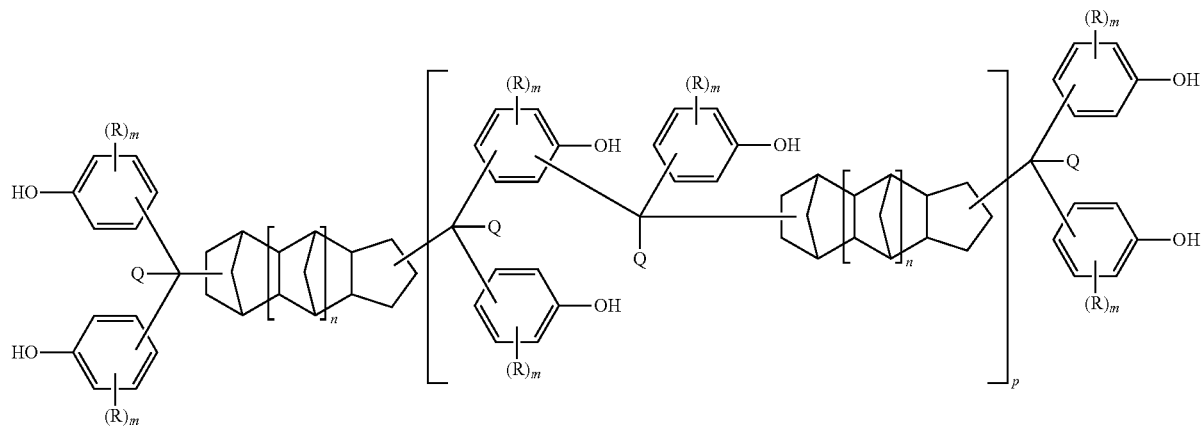

(Formula VIII)

where R, m, Q, n, and p are as described herein. As discussed herein, polycyclopentadiene diphenols and/or oligomers may also be present with the polycyclopentadiene polyphenols.

bromohydrin, methylepiiodohydrin and combinations thereof. Most preferred as the epihalohydrin is epichlorohydrin.

A suitable basic acting substance is employed to prepare the polycyclopentadiene compounds of the present disclosure. Suitable basic acting substances include, for example, the alkali metal or alkaline earth metal hydroxides, carbonates and bicarbonates, and combinations thereof. Particularly suitable compounds include sodium hydroxide, potassium hydroxide, lithium hydroxide, calcium hydroxide, barium hydroxide, magnesium hydroxide, manganese hydroxide, sodium carbonate, potassium carbonate, lithium carbonate, calcium carbonate, barium carbonate, magnesium carbonate, manganese carbonate, sodium bicarbonate, potassium bicarbonate, magnesium bicarbonate, lithium bicarbonate, calcium bicarbonate, barium bicarbonate, manganese bicarbonate and combinations thereof. Most preferred is sodium hydroxide or potassium hydroxide. For processes involving reaction of the polycyclopentadiene polyphenol and/or diphenol with an alkali metal hydride followed by reaction with the epihalohydrin, suitable alkali metal hydrides include, for example, sodium hydride and potassium hydride, with sodium hydride being most preferred.

For the various embodiments, suitable catalysts that can be employed to prepare the polycyclopentadiene compounds of the present disclosure include, for example, the ammonium or phosphonium halides, such as, for example, benzyltrimethylammonium chloride, benzyltrimethylammonium bromide, tetrabutylammonium chloride, tetrabutylammonium bromide, tetraoctylammonium chloride, tetrabutylammonium bromide, tetramethylammonium chloride, tetramethylammonium bromide, tetrabutylphosphonium chloride, tetrabutylphosphonium bromide, tetrabutylphosphonium iodide, ethyltriphenylphosphonium chloride, ethyltriphenylphosphonium bromide, ethyltriphenylphosphonium iodide and combinations thereof.

For the various embodiments, suitable solvents that can be employed to prepare the polycyclopentadiene compounds of the present disclosure include aliphatic and aromatic hydrocarbons, aliphatic secondary alcohols, halogenated aliphatic hydrocarbons, aliphatic ethers, aliphatic nitriles, cyclic ethers, ketones, amides, sulfoxides, and combinations thereof. Particularly suitable solvents include pentane, hexane, octane, toluene, xylene, methylethylketone, methylisobutylketone, N,N-dimethylformamide, dimethylsulfoxide, diethyl ether, tetrahydrofuran, 1,4-dioxane, dichloromethane, chloroform, ethylene dichloride, methyl chloroform, ethylene glycol dimethyl ether, N,N-dimethylacetamide, acetonitrile, isopropanol, isobutanol, propylene glycol monomethyl ether, and combinations thereof. The solvent may be removed at the completion of the reaction using conventional means, such as, for example, vacuum distillation. One possible process for preparing the polycyclopentadiene compounds of the present disclosure is done in the absence of a solvent, where the epihalohydrin being used in the reaction, such as epichlorohydrin, is used in an amount to function as both the solvent and reactant.

Analytical methods, such as high pressure liquid chromatography (HPLC), may be employed to monitor reaction of the polycyclopentadiene polyphenol and/or diphenol concurrently with the formation of intermediate product, such as the halohydrin, and the final polycyclopentadiene compounds of the present disclosure.

Recovery and purification of the polycyclopentadiene compounds of the present disclosure can be performed using a variety of methods. For example, gravity filtration, vacuum filtration, centrifugation, water washing or extraction, solvent extraction, decantation, column chromatography, vacuum distillation, falling film distillation, electrostatic coalescence, and other processing methods and the like may be used.

Vacuum distillation is a most preferred method for removal and recovery of lighter boiling fractions, for example, unused epihalohydrin. This recovers epichlorohydrin for recycle.

Oligomers may also be present in the polycyclopentadiene compounds of the present disclosure. These typically arise from an epoxidation of oligomeric components present in the polycyclopentadiene polyphenol and/or diphenol precursor or from the in situ advancement reaction of a portion of the glycidyl ether moieties. Advancement is characterized by the formation of the 2-hydroxypropyl ether linkage (the structure of Formula IX) in the epoxy resin product:

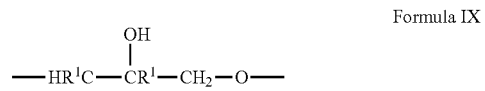

Formula IX

The polycyclopentadiene compounds of the present disclosure, as well as blends thereof with conventional epoxy resins, may be used to prepare advanced epoxy resins (thermosettable resins) and/or vinyl esters and vinyl ester resins. For example, embodiments of the present disclosure can include blends, partially polymerized (B-staged) products, or cured (thermoset) products of the polycyclopentadiene compounds of the present disclosure with a bis or poly(maleimide); a di or polycyanate; a di or polycyanamide; an epoxy resin; a polymerizable mono, di, or poly(ethylenically unsaturated) monomer, including vinyl benzyl ethers, allyl and allyloxy compounds and combinations thereof.

The polycyclopentadiene compounds of the present disclosure may also be formulated with other resins, such as, but not limited to polyurethane resins, polyester resins, epoxy resins (e.g., as provided herein), and combinations thereof. In additional embodiments, the polycyclopentadiene compounds of the present disclosure can also be employed as co-monomers with other thermosettable monomers.

For the various embodiments, the polycyclopentadiene compounds of the present disclosure can also be used in forming adducts useful as (a) epoxy resin curing agents, (b) reactants for thermoset polyurethanes, polyureaurethanes, and polyisocyanurates and (c) initiators for polyols useful in preparation of polyurethanes, polyureaurethanes, polyisocyanurates.

The polycyclopentadiene compounds of the present disclosure, beside other things, may be useful in preparing cured compositions for use in structural or electrical laminates and/or composites, multilayer electronic circuitry, integrated circuit packaging (such as "IC substrates"), filament windings, moldings, encapsulations, castings, composites for aerospace applications, and adhesives. Additionally, the polycyclopentadiene compounds of the present disclosure may find utility as highly functional epoxy resin curing agents useful, for example, in coatings, such as functional powder coatings and other protective coatings, where the need for a high glass transition temperature, solvent resistance, abrasion resistance and/or toughness may be beneficial. The cured compositions of the present disclosure may also be used in the form of sheets, films, fibers or other shaped articles.

Adducts of the Polycyclopentadiene Compounds

Embodiments of the present disclosure further include adducts prepared using the polycyclopentadiene compounds of the present disclosure. For the various embodiments, preparing adducts with the polycyclopentadiene compounds of the present disclosure allows for the physical and the mechanical property advantages of the polycyclopentadienyl structure, as well as the physical and mechanical property advantages imparted by the high degree of functionality to be combined into the adduct. Thus, enhanced glass transition temperatures, high temperature resistance, improved moisture resistance and corrosion resistance, as well as enhanced electrical properties, especially dissipation factor, are expected as a result of the polycyclopentadienyl structure when the adducts are used in the formation of thermosets (including both epoxy or polyurethane types).

For the various embodiments, the adducts of the present disclosure can be prepared by reaction of one or more of the polycyclopentadiene compounds of the present disclosure (e.g., the compounds of Formula I, of Formula III, and combinations thereof) with one or more hydrogen containing compounds possessing one or more hydrogen atoms per molecule that are reactive with epoxide groups, such as those epoxide groups contained in the polycyclopentadiene compounds of the present disclosure.

Proposed end uses for the adducts include bisphenol A-free applications, curing agents for epoxy resin based coatings, especially decorative and functional powder coatings and other protective coatings with weatherability, solvent resistance, moisture resistance, abrasion resistance, and toughness; curing agents for epoxy resins based electrical or structural laminates or composites; filament windings; moldings; castings; encapsulation; multilayer electronic circuitry, integrated circuit packaging (such as "IC substrates"); composites for aerospace; adhesives; and in compositions with other curing agents or resin blends such as, for example, polymaleimides and polycyanates blends with one or more epoxy resins.

Further proposed uses for the adducts of the present disclosure include the preparation of thermoset polyurethanes that may be cellular (foam) or non-cellular and may additionally include additives including, for example, fillers, pigments, dyes, flow modifiers, thickeners, reinforcing agents, mold release agents, wetting agents, stabilizers, fire retardant agents, surfactants and combination thereof. The thermoset polyurethanes prepared using the adducts of the present disclosure may be useful in the preparation of castings, moldings coatings, structural foams, flexible foams, rigid foams, and insulation among other structures. Polyisocyanurate foams represent a special class of rigid foams that may be prepared using the adducts of the present disclosure. Polyisocyanurate foams are generally prepared by the catalytic trimerization of a polyisocyanate and the adduct of the present disclosure.

The adducts of the present disclosure may also be used as initiators for polyols useful in preparing polyurethanes, polyureaurethanes, and/or polyisocyanurates. Additionally, the adducts may be reacted to provide compositions that may then be used to prepare the polyol initiators.

Hydrogen Containing Compound

The hydrogen containing compound used in the present disclosure to react with the polycyclopentadiene compounds of Formula I and/or Formula III to form the adduct includes one or more reactive hydrogen atoms per molecule. The reactive hydrogen atoms are reactive with epoxide groups, such as those epoxide groups (Formula II) contained in the polycyclopentadiene compounds of Formula I and Formula III.

The term "reactive hydrogen atom" as used herein means that the hydrogen atom is reactive with an epoxide group. The reactive hydrogen atom differs from other hydrogen atoms including those hydrogen atoms which are non-reactive with epoxide groups in the reaction of forming the adduct, but may be reactive with epoxide groups in a later process of curing the adduct with one or more epoxy resins.

For the various embodiments, hydrogen atoms can be non-reactive with the epoxide groups in the process of forming the adduct, but reactive in a later process of curing the adduct. For example, such reactions in the later process can be with an epoxy resin having other functional groups that are more reactive with the epoxide groups under the curing reaction conditions used as compared to the reaction conditions used in the reaction of forming the adduct. For example, a hydrogen containing compound may have two different functional groups each bearing at least one reactive hydrogen atom, with one functional group being inherently more reactive with an epoxide group than the other under the reaction conditions used. These reaction conditions may include the use of a catalyst that favors a reaction of the reactive hydrogen atom(s) of one functional group with an epoxide group over a reaction of the reactive hydrogen atom(s) of the other functional group with an epoxide group.

Other non-reactive hydrogen atoms may also include hydrogen atoms in the secondary hydroxyl groups (Formula IX) that form during an epoxide ring opening reaction in the process of producing the adduct. However, for use in preparation of thermosettable polyurethane compositions, the secondary hydroxyl groups are considered as reactive hydrogen atoms.

The hydrogen containing compound that includes the one or more reactive hydrogen atoms per molecule may further include aliphatic, cycloaliphatic or aromatic groups within the hydrogen containing compound. The aliphatic groups may be branched or unbranched. The aliphatic or cycloaliphatic groups may also be saturated or unsaturated and may include one or more substituents that are inert (not reactive) to the process of preparing the adduct of the present disclosure including the reactants and the products. The substituents may be attached to a terminal carbon atom or may be between two carbon atoms, depending on the chemical structures of the substituents. Examples of such inert substituents include halogen atoms, preferably chlorine or bromine, nitrile, nitro, alkyloxy, keto, ether (—O—), thioether (—S—), or tertiary amine. The aromatic ring, if present within the hydrogen containing compound structure, may include one or more heteroatoms such as N, O, S and the like.

Examples of the hydrogen containing compound may include compounds such as (a) di- and polyphenols, (b) di- and polycarboxylic acids, (c) di- and polymercaptans, (d) di- and polyamines, (e) primary monoamines, (f) sulfonamides, (g) aminophenols, (h) aminocarboxylic acids, (i) phenolic hydroxyl containing carboxylic acids, (j) sulfanilamides, (k) mono-functional phosphorous compounds and (l) combinations of two or more of such compounds or the like.

Examples of the di- and polyphenols (a) include 1,2-dihydroxybenzene (catechol); 1,3-dihydroxybenzene (resorcinol); 1,4-dihydroxybenzene (hydroquinone); 4,4'-isopropylidenediphenol (bisphenol A); 4,4'-dihydroxydiphenylmethane; 3,3',5,5'-tetrabromobisphenol A; 4,4'-thiodiphenol; 4,4'-sulfonyldiphenol; 2,2'-sulfonyldiphenol; 4,4'-dihydroxydiphenyl oxide; 4,4'-dihydroxybenzophenone; 1,1'-bis(4-hydroxyphenyl)-1-phenylethane; 3,3', 5,5'-tetrachlorobisphenol A; 3,3'-dimethoxybisphenol A; 3,3',5,5'-tetramethyl-4,4'-dihydroxydiphenyl; 4,4'-dihydroxybiphenyl; 4,4'-dihydroxy-alpha-Methylstilbene; 4,4'-dihydroxybenzanilide; 4,4'-dihydroxystilbene; 4,4'-dihydroxy-alpha-cyanostilbene; 1,1-bis(4-hydroxyphenyl) cyclohexane; 1,4-dihydroxy-3,6-dimethylbenzene; 1,4-dihydroxy-3,6-dimethoxybenzene; 1,4-dihydroxy-2-tert-butylbenzene; 1,4-dihydroxy-2-bromo-5-methylbenzene; 1,3-dihydroxy-4-nitrophenol; 1,3-dihydroxy-4-cyanophenol; tris(hydroxyphenyl)methane; dicyclopentadiene or an oligomer thereof and phenol or substituted phenol condensation products and combinations thereof.

Examples of the di- and polycarboxylic acids (b) include 4,4'-dicarboxydiphenylmethane; terephthalic acid; isophthalic acid; 1,4-cyclohexanedicarboxylic acid; 1,6-hexanedicarboxylic acid; 1,4-butanedicarboxylic acid; dicyclopentadienedicarboxylic acid; tris(carboxyphenyl)methane; 1,1-bis (4-carboxyphenyl)cyclohexane; 3,3',5,5'-tetramethyl-4,4'-dicarboxydiphenyl; 4,4'-dicarboxy-alpha-methylstilbene; 1,4-bis(4-carboxyphenyl)-trans-cyclohexane; 1,1'-bis(4-carboxyphenyl)cyclohexane; 1,3-dicarboxy-4-methylbenzene; 1,3-dicarboxy-4-methoxybenzene; 1,3-dicarboxy-4-bromobenzene and combinations thereof.

Examples of the di- and polymercaptans (c) include 1,3-benzenedithiol; 1,4-benzenedithiol; 4,4'-dimercaptodiphenylmethane; 4,4'-dimercaptodiphenyl oxide; 4,4'-dimercapto-alpha-methylstilbene; 3,3',5,5'-tetramethyl-4,4'-dimercaptodiphenyl; 1,4-cyclohexanedithiol; 1,6-hexanedithiol; 2,2'-dimercaptodiethylether; 1,2-dimercaptopropane; bis(2-mercaptoethyl)sulfide; tris (mercaptophenyl)methane; 1,1-bis(4-mercaptophenyl) cyclohexane and combinations thereof.

Examples of the di- and polyamines (d) include 1,2-diaminobenzene; 1,3-diaminobenzene; 1,4-diaminobenzene; 4,4'-diaminodiphenylmethane; 4,4'-diaminodiphenylsulfone; 2,2'-diaminodiphenylsulfone; 4,4'-diaminodiphenyl oxide; 3,3',5,5'-tetramethyl-4,4'-diaminodiphenyl; 3,3'-dimethyl-4,4-diaminodiphenyl; 4,4'-diamino-alpha-methylstilbene; 4,4'-diaminobenzanilide; 4,4'-diaminostilbene; 1,4-bis(4-aminophenyl)-trans-cyclohexane; 1,1-bis(4-aminophenyl) cyclohexane; tris(aminophenyl)methane; 1,4-cyclohexanediamine; 1,6-hexanediamine; piperazine; ethylenediamine; diethyletriamine; triethylenetetramine; tetraethylenepentamine; 1-(2-aminoethyl)piperazine; bis(aminopropyl)ether; bis(aminopropyl)sulfide; bis(aminomethyl) norbornane, 2,2'-bis(4-aminocyclohexyl)propane and combinations thereof.

Examples of the primary monoamines (e) include aniline; 4-chloroaniline; 4-methylaniline; 4-methoxyaniline; 4-cyanoaniline; 2,6-dimethylaniline; 4-aminodiphenyl oxide; 4-aminodiphenylmethane; 4-aminodiphenylsulfide; 4-aminobenzophenone; 4-aminodiphenyl; 4-aminostilbene; 4-amino-alpha-methylstilbene; methylamine; 4-amino-4'-nitrostilbene; n-hexylamine; cyclohexylamine; aminonorbornane and combinations thereof.

Ammonia represents a special class of hydrogen containing compound of the present disclosure. The ammonia may be used in the form of liquefied ammonia ($NH_3$) and/or ammonium hydroxide ($NH_4OH$).

Examples of the sulfonamides (f) include phenylsulfonamide; 4-methoxyphenylsulfonamide; 4-chlorophenylsulfonamide; 4-bromophenylsulfonamide; 4-methylsulfonamide; 4-cyanosulfonamide; 2,6-dimethyphenylsulfonamide; 4-sulfonamidodiphenyl oxide; 4-sulfonamidodiphenylmethane; 4-sulfonamidobenzophenone; 4-sulfonylamidodiphenyl; 4-sulfonamidostilbene; 4-sulfonamido-alpha-methylstilbene and combinations thereof.

Examples of the aminophenols (g) include o-aminophenol; m-aminophenol; p-aminophenol; 2-methoxy-4-hydroxyaniline; 3,5-dimethyl-4-hydroxyaniline; 3-cyclohexyl-4-hydroxyaniline; 2,6-dibromo-4-hydroxyaniline; 5-butyl-4-hydroxyaniline; 3-phenyl-4-hydroxyaniline; 4-(1-(3-aminophenyl)-1-methylethyl)phenol; 4-(1-(4-aminophenyl) ethyl)phenol; 4-(4-aminophenoxy)phenol; 4-((4-aminophenyl)thio)phenol; (4-aminophenyl)(4-hydroxyphenyl)methanone; 4-((4-aminophenyl)sulfonyl) phenol; 4-(1-(4-amino-3,5-dibromophenyl)-1-methyl ethyl)-2,6-dibromophenol; N-methyl-p-aminophenol; 4-amino-4'-hydroxy-alpha-methylstilbene; 4-hydroxy-4'-amino-alpha-methylstilbene and combinations thereof.

Examples of the aminocarboxylic acids (h) include 2-aminobenzoic acid; 3-aminobenzoic acid; 4-aminobenzoic acid; 2-methoxy-4-aminobenzoic acid; 3,5-dimethyl-4-aminobenzoic acid; 3-cyclohexyl-4-aminobenzoic acid; 2,6-dibromo-4-aminobenzoic acid; 5-butyl-4-aminobenzoic acid; 3-phenyl-4-aminobenzoic acid; 4-(1-(3-aminophenyl)-1-methylethyl)benzoic acid; 4-(1-(4-aminophenyl)ethyl) benzoic acid; 4-(4-aminophenoxy)benzoic acid; 4-((4-aminophenyl)thio)benzoic acid; (4-aminophenyl)(4-carboxyphenyl)methanone; 4-((4-aminophenyl)sulfonyl) benzoic acid; 4-(1-(4-amino-3,5-dibromophenyl)-1-methylethyl)-2,6-dibromobenzoic acid; N-methyl-4-aminobenzoic acid; 4-amino-4'-carboxy-alpha-methylstilbene; 4-carboxy-4'-amino-alpha-methylstilbene; glycine; N-methylglycine; 4-aminocyclohexanecarboxylic acid; 4-aminohexanoic acid; 4-piperidinecarboxylic acid; 5-aminophthalic acid and combinations thereof.

Examples of the phenolic hydroxyl containing carboxylic acids (i) include 2-hydroxybenzoic acid; 3-hydroxybenzoic acid; 4-hydroxybenzoic acid; 2-methoxy-4-hydroxybenzoic acid; 3,5-dimethyl-4-hydroxybenzoic acid; 3-cyclohexyl-4-hydroxybenzoic acid; 2,6-dibromo-4-hydroxybenzoic acid; 5-butyl-4-hydroxybenzoic acid; 3-phenyl-4-hydroxybenzoic acid; 4-(1-(3-hydroxyphenyl)-1-methylethyl)benzoic acid; 4-(1-(4-hydroxyphenyl)ethyl)benzoic acid; 4-(4-hydroxyphenoxy)benzoic acid; 4-((4-hydroxyphenyl)thio)benzoic acid; (4-hydroxyphenyl)(4-carboxyphenyl)methanone; 4-((4-hydroxyphenyl)sulfonyl)benzoic acid; 4-(1-(4-hydroxy-3,5-dibromophenyl)-1-methylethyl)-2,6-dibromobenzoic acid; 4-hydroxy-4'-carboxy-alpha-methylstilbene; 4-carboxy-4'-hydroxy-alpha-methylstilbene; 2-hydroxyphenylacetic acid; 3-hydroxyphenylacetic acid; 4-hydroxyphenylacetic acid; 4-hydroxyphenyl-2-cyclohexanecarboxylic acid; 4-hydroxyphenoxy-2-propanoic acid and combinations thereof.

Examples of the sulfanilamides (j) include o-sulfanilamide; m-sulfanilamide; p-sulfanilamide; 2-methoxy-4-aminobenzoic acid; 2,6-dimethyl-4-sulfonamido-1-aminobenzene; 3-methyl-4-sulfonamido-1-aminobenzene; 5-methyl-3-sulfonamido-1-aminobenzene; 3-phenyl-4-sulfonamido-1-aminobenzene; 4-(1-(3-sulfonamidophenyl)-1-methylethyl)aniline; 4-(1-(4-sulfonamidophenyl)ethyl) aniline; 4-(4-sulfonamidophenoxy)aniline; 4-((4-sulfonamidophenyl)thio)aniline; (4-sulfonamidophenyl)(4-aminophenyl)methanone, 4-((4-sulfonamidophenyl) sulfonyl)aniline; 4-(1-(4-sulfonamido-3,5-dibromophenyl)-1-methylethyl)-2,6-dibromoaniline; 4-sulfonamido-1-N-methylaminobenzene; 4-amino-4'-sulfonamido-alpha-methylstilbene; 4-sulfonamido-4'-amino-alpha-methylstilbene and combinations thereof.

Examples of the (k) mono-functional phosphorous compounds include 9,10-dihydro-9-oxa-10-phosphaphenanthrene-10-oxide (also known as DOP); 1,3,2-dioxaphosphorinane, 2-hydroxy-5,5-dimethyl-; 1,3,2-dioxaphosphorinane; 1,3,2-dioxaphospholane; 1,3,2-dioxaphospholane, 2-oxide, 5,5-dimethyl-; 1,3,2-benzodioxaphosphole, 2-oxide; 1,3,2-benzodioxaphosphole; 1,3,2-diazaphospholidine, 1,3-dimethyl-; 1,3,2-diazaphospholidine, and 1,3-dimethyl-, 2-oxide, among others. Additional examples of mono-functional phosphorous compounds can also be found in WO 2005/118604 to Gan, which is incorporated herein by reference.

Resin Formulations

In another aspect of the present disclosure, the adduct of the present disclosure may additionally be formed from at least one reaction product of an (1) the polycyclopentadiene compounds epoxy of Formula I and/or Formula III, (2) the hydrogen containing compound, and (3) a resin compound, where the resin compound includes one or more epoxy resins other than the polycyclopentadiene compounds of Formula I and/or Formula III.

The epoxy resin that can be used as the resin compound other than the polycyclopentadiene compounds of the present disclosure can be an epoxide-containing compound having an average of more than one epoxide group per molecule. The epoxide group can be attached to an oxygen, a sulfur or a nitrogen atom or the single bonded oxygen atom attached to the carbon atom of a —CO—O— group. The oxygen, sulfur, nitrogen atom, or the carbon atom of the —CO—O— group may be attached to an aliphatic, cycloaliphatic, polycycloaliphatic or aromatic hydrocarbon group. The aliphatic, cycloaliphatic, polycycloaliphatic or aromatic hydrocarbon group can be substituted with an inert substituents including, but not limited to, halogen atoms, preferably fluorine, bromine or chlorine; nitro groups; or the groups can be attached to the terminal carbon atoms of a compound containing an average of more than one —(O—CHR$^a$—CHR$^a$)$_t$— group, where each R$^a$ is independently a hydrogen atom, an alkyl, or a haloalkyl group containing from one to two carbon atoms, with the proviso that only one R$^a$ group can be a haloalkyl group, and t has a value from one to about 100, preferably from one to about 20, more preferably from one to about 10, and most preferably from one to about 5.

More specific examples of the epoxy resin which can be used as the resin compound include diglycidyl ethers of 1,2-dihydroxybenzene (catechol); 1,3-dihydroxybenzene (resorcinol); 1,4-dihydroxybenzene (hydroquinone); 4,4'-isopropylidenediphenol (bisphenol A); 4,4'-dihydroxydiphenylmethane; 3,3',5,5'-tetrabromobisphenol A; 4,4'-thiodiphenol; 4,4'-sulfonyldiphenol; 2,2'-sulfonyldiphenol; 4,4'-dihydroxydiphenyl oxide; 4,4'-dihydroxybenzophenone; 1,1'-bis(4-hydroxyphenyl)-1-phenylethane; 3,3'-5,5'-tetrachlorobisphenol A; 3,3'-dimethoxybisphenol A; 4,4'-dihydroxybiphenyl; 4,4'-dihydroxy-alpha-methylstilbene; 4,4'-dihydroxybenzanilide; 4,4'-dihydroxystilbene; 4,4'-dihydroxy-alpha-cyanostilbene; N,N'-bis(4-hydroxyphenyl)terephthalamide; 4,4'-dihydroxyazobenzene; 4,4'-dihydroxy-2,2'-dimethylazoxybenzene; 4,4'-dihydroxydiphenylacetylene; 4,4'-dihydroxychalcone; 4-hydroxyphenyl-4-hydroxybenzoate; dipropylene glycol; polypropylene glycol); thiodiglycol; the triglycidyl ether of tris(hydroxyphenyl)methane; the polyglycidyl ethers of a phenol or alkyl or halogen substituted phenol-aldehyde acid catalyzed condensation product (novolac resins); the tetraglycidyl amines of 4,4'-diaminodiphenylmethane; 4,4'-diaminostilbene; N,N'-dimethyl-4,4'-diaminostilbene; 4,4'-diaminobenzanilide; 4,4'-diaminobiphenyl; the polyglycidyl ether of the condensation product of a dicyclopentadiene or an oligomer thereof and a phenol or alkyl or halogen substituted phenol; and combinations thereof.

The epoxy resin which can be used as the resin compound may also include an advanced epoxy resin. The advanced epoxy resin may be a product of an advancement reaction of an epoxy resin with an aromatic di- and polyhydroxyl, or carboxylic acid containing compound. The epoxy resin used in the advancement reaction may include one or more of the aforesaid epoxy resins suitable for the resin compound comprising the di- or polyglycidyl ethers.

Examples of the aromatic di- and polyhydroxyl or carboxylic acid containing compound include hydroquinone; resorcinol; catechol; 2,4-dimethylresorcinol; 4-chlororesorcinol; tetramethylhydroquinone; bisphenol A; 4,4'-dihydroxydiphenylmethane; 4,4'-thiodiphenol; 4,4'-sulfonyldiphenol; 2,2'-sulfonyldiphenol; 4,4'-dihydroxydiphenyl oxide; 4,4'-dihydroxybenzophenone; 1,1-bis(4-hydroxyphenyl)-1-phenylethane; 4,4'-bis(4(4-hydroxyphenoxy)-phenylsulfone)diphenyl ether; 4,4'-dihydroxydiphenyl disulfide; 3,3',3,5'-tetrachloro-4,4'-isopropylidenediphenol; 3,3',3,5'-tetrabromo-4,4'-isopropylidenediphenol; 3,3'-dimethoxy-4,4'-isopropylidenediphenol; 4,4'-dihydroxybiphenyl; 4,4'-dihydroxy-alpha-methylstilbene; 4,4'-dihydroxybenzanilide; bis(4-hydroxyphenyl)terephthalate; N,N'-bis(4-hydroxyphenyl)terephthalamide; bis(4'-hydroxybiphenyl)terephthalate; 4,4'-dihydroxyphenylbenzoate; bis(4'-hydroxyphenyl)-1,4-benzenediimine; 1,1'-bis(4-hydroxyphenyl)cyclohexane; phloroglucinol; pyrogallol; 2,2',5,5'-tetrahydroxydiphenylsulfone; tris(hydroxyphenyl)methane; dicyclopentadiene diphenol; tricyclopentadienediphenol; terephthalic acid; isophthalic acid; 4,4'-benzanilidedicarboxylic acid; 4,4'-phenylbenzoatedicarboxylic acid; 4,4'-stilbenedicarboxylic acid; adipic acid and combinations thereof.

Preparation of the aforementioned advanced epoxy resin products can be performed using known methods, for example, an advancement reaction of an epoxy resin with one or more suitable compounds having an average of more than one reactive hydrogen atom per molecule, where the reactive hydrogen atom is reactive with an epoxide group in the epoxy resin.

The ratio of the compound having an average of more than one reactive hydrogen atom per molecule to the epoxy resin is generally from about 0.01:1 to about 0.95:1, preferably from about 0.05:1 to about 0.8:1, and more preferably from about 0.10:1 to about 0.5:1 equivalents of the reactive hydrogen atom per equivalent of the epoxide group in the epoxy resin.

In addition to the aforementioned dihydroxyaromatic and dicarboxylic acid compounds, examples of the compound having an average of more than one reactive hydrogen atom per molecule may also include dithiol, disulfonamide or compounds containing one primary amine or amide group, two secondary amine groups, one secondary amine group and one phenolic hydroxy group, one secondary amine group and one carboxylic acid group, or one phenolic hydroxy group and one carboxylic acid group, and combinations thereof.

The advancement reaction may be conducted in the presence or absence of a solvent with the application of heat and mixing. The advancement reaction may be conducted at atmospheric, superatmospheric or subatmospheric pressures and at temperatures of from about 20° C. to about 260° C., preferably, from about 80° C. to about 240° C., and more preferably from about 100° C. to about 200° C.

The time required to complete the advancement reaction depends upon the factors such as the temperature employed, the chemical structure of the compound having more than one reactive hydrogen atom per molecule employed, and the chemical structure of the epoxy resin employed. Higher temperature may require shorter reaction time whereas lower temperature requires a longer period of reaction time. In general, the time for completion of the advancement reaction may range from about 5 minutes to about 24 hours, preferably from about 30 minutes to about 8 hours, and more preferably from about 30 minutes to about 4 hours.

A catalyst may also be added in the advancement reaction. Examples of the catalyst may include phosphines, quaternary ammonium compounds, phosphonium compounds and tertiary amines. The catalyst may be employed in quantities of from about 0.01 percent to about 3 percent, preferably from about 0.03 percent to about 1.5 percent, and more preferably from about 0.05 percent to about 1.5 percent by weight based upon the total weight of the epoxy resin.

Other details concerning an advancement reaction useful in preparing the advanced epoxy resin product for the resin compound of the present disclosure are provided in U.S. Pat. No. 5,736,620 and in the aforementioned Handbook of Epoxy Resins by Henry Lee and Kris Neville, incorporated herein by reference.

Adduct

The adduct of the present disclosure is a reaction product of the polycyclopentadiene compounds of the present disclosure, the hydrogen containing compound and, optionally, the resin compound.

According to the present disclosure, a sufficient amount of the polycyclopentadiene compound and the resin compound, if used, and an excess amount of the hydrogen containing compound are provided in a reaction mixture to form the adduct of the present disclosure. At the end of the reaction for forming the adduct of the present disclosure (also referred as "the adduct forming reaction"), essentially all of the epoxide groups in the polycyclopentadiene compounds of the present disclosure are reacted with the reactive hydrogen atoms in the hydrogen containing compound. The unreacted hydrogen containing compound may be removed partially or completely at the end of the reaction or may remain as a part of the adduct product.

In general, the ratio of the hydrogen containing compound and the polycyclopentadiene compound is from about 2:1 to about 200:1, preferably from about 3:1 to about 100:1, and more preferably from about 4:1 to about 50:1 equivalents of the reactive hydrogen atom in the hydrogen containing compound per equivalent of epoxide group in the polycyclopentadiene compounds and, if used, resin compound.

A catalyst may be employed to prepare the adduct of the present disclosure. Examples of the catalyst include phosphines, quaternary ammonium compounds, phosphonium compounds, tertiary amines and combinations thereof. The amount of catalyst used, if any, depends upon the particular reactants used for preparing the adduct and the type of catalyst employed. In general, the catalyst may be used in an amount of from about 0.01 to about 1.5 percent, and preferably from about 0.03 to about 0.75 percent by weight based on the total weight of the adduct.

One or more solvents may be present in the adduct forming reaction of the present disclosure. The presence of a solvent or solvents can improve the solubility of the reactants or, if the reactant is in a solid foil, dissolve the solid reactant for easy mixing with other reactants. The presence of the solvent may also dilute the concentration of the reactants in order to moderate the adduct forming reaction such as to control heat generated from the adduct forming reaction or to lower the effective concentration of a reactant which can in turn influence the structure of the adduct product, for example, produce an adduct with less oligomeric component.

The solvent may be substantially inert to the adduct forming reaction including inert to the reactants, the intermediate products if any, and the final products. Examples of suitable solvents useful in the present disclosure include aliphatic, cycloaliphatic and aromatic hydrocarbons, halogenated aliphatic and cycloaliphatic hydrocarbons, aliphatic and cycloaliphatic secondary alcohols, aliphatic ethers, aliphatic nitriles, cyclic ethers, glycol ethers, esters, ketones, amides, sulfoxides and combinations thereof. Preferred examples of the solvents include pentane, hexane, octane, cyclohexane, methylcyclohexane, toluene, xylene, methylethylketone, methylisobutylketone, cyclohexanone, N,N-dimethylformamide, dimethylsulfoxide, diethyl ether, tetrahydrofuran, 1,4-dioxane, dichloromethane, chloroform, ethylene dichloride, methyl chloroform, ethylene glycol dimethyl ether, N,N-dimethylacetamide, acetonitrile, isopropanol and combinations thereof.

The solvent may be removed at the completion of the adduct forming reaction using conventional means, such as, for example, vacuum distillation. Alternatively, the solvent may also be left in the adduct product to provide a solvent borne adduct which may be used later, for example, in the preparation of coating or film.

The adduct forming reaction conditions may vary depending upon factors such as types and amounts of reactants employed, type and amount of catalyst used, if any, type and amount of solvent used, if any, and modes of addition of the reactants employed. For example, the adduct fanning reaction may be conducted at atmospheric (e.g. 760 mm Hg), superatmospheric or subatmospheric pressures and at temperature of from about 0° C. to about 260° C., and preferably from about 20° C. to about 200° C., and more preferably from about 35° C. to about 160° C.

The time required to complete the adduct forming reaction depends not only upon the aforementioned factors, but also upon the temperature employed. Higher temperature requires a shorter period of time, whereas lower temperature requires a longer period of time. In general, the time to complete the adduct forming reaction is preferred to be from about 5 minutes to about one week, more preferably from about 30 minutes to about 72 hours, and most preferably from about 60 minutes to 48 hours.

The time and temperature of the adduct forming reaction may have significant impact on the distribution of components in the formation of the adduct of the present disclosure. For example, with higher reaction temperature, longer reaction time, and when the hydrogen containing compound includes a material having only two reactive hydrogen atoms per molecule, the adduct forming reaction favors the formation of the adduct with more oligomeric components. The adduct forming reaction favors the formation of the adduct with more branched or crosslinked components when the hydrogen containing compound includes a material having more than two reactive hydrogen atoms per molecule.

In carrying out the adduct forming reaction, the polycyclopentadiene compounds of the present disclosure may be directly mixed together with the hydrogen containing compound, added to the hydrogen containing compound in incremental steps, or added to the hydrogen containing compound continuously. In addition, one or more solvents may be first added to the polycyclopentadiene compounds and/or the hydrogen containing compound before mixing the polycyclopentadiene compounds and the hydrogen containing compound. If incremental addition of the polycyclopentadiene compounds is used, all or a part of an added increment may be allowed to react prior to addition of the next increment. The incremental addition of the polycyclopentadiene compounds reacted within an excess amount of the hydrogen containing compound generally favors the formation of the adduct with a lesser amount or free of oligomeric components.

Various post treatments may be applied to the process of preparing the adduct of the present disclosure in order to modify: 1) the distribution of the amounts of individual components of the adduct, 2) the reactivity of the adduct, and/or 3) the physical properties of the adduct.

For example, for an adduct prepared from a reaction between the polycyclopentadiene compounds and cyclohexylamine (as the hydrogen containing compound), when a large stoichiometric excess amount of the primary amine groups derived from the cyclohexylamine reacts with the epoxide groups derived from the polycyclopentadiene compounds, the reaction may lead to the formation of an adduct with a low content of oligomeric component. The resultant adduct product may also include, as a part of the adduct product, a high concentration of cyclohexylamine as the unreacted hydrogen containing compound. Accordingly, post treatment of the adduct product, such as vacuum distillation, may be employed to strip out the unreacted hydrogen containing compound.

Other post treatment methods used to modify the distribution of the adduct components may also be employed, such as, for example, recrystallization, chromatographic separation, extraction, zone refining, crystal refining, falling film distillation, wiped film distillation, simple distillation, including rotary evaporation, preferential chemical derivatization and removal of one or more components of the adduct, and combinations thereof.

According to the present disclosure, the reaction of one of more of the polycyclopentadiene compounds and/or advancement products (oligomers) with one or more hydrogen containing compounds possessing hydrogen atoms which are reactive with epoxide groups to faun the adduct of the present disclosure involves a ring opening reaction. During the ring opening reaction, the epoxide groups in the epoxy resin reacts with the reactive hydrogen atoms in the hydrogen containing compound to give characteristic 2-hydroxylpropyl functionalities as linkages between residual structures of the epoxy resin and residual structures of the hydrogen containing compound.

An example of the adduct of the present disclosure is a reaction product of polyglycidyl ethers of Formula I and/or Formula III and cyclohexylamine (as the hydrogen containing compound). The following idealized adduct structure of Formula X shows the 2-hydroxylpropyl functionality as the linkage between the residual structure of the epoxy resin of Formula I and the residual structure of the hydrogen containing compound:

Formula X:

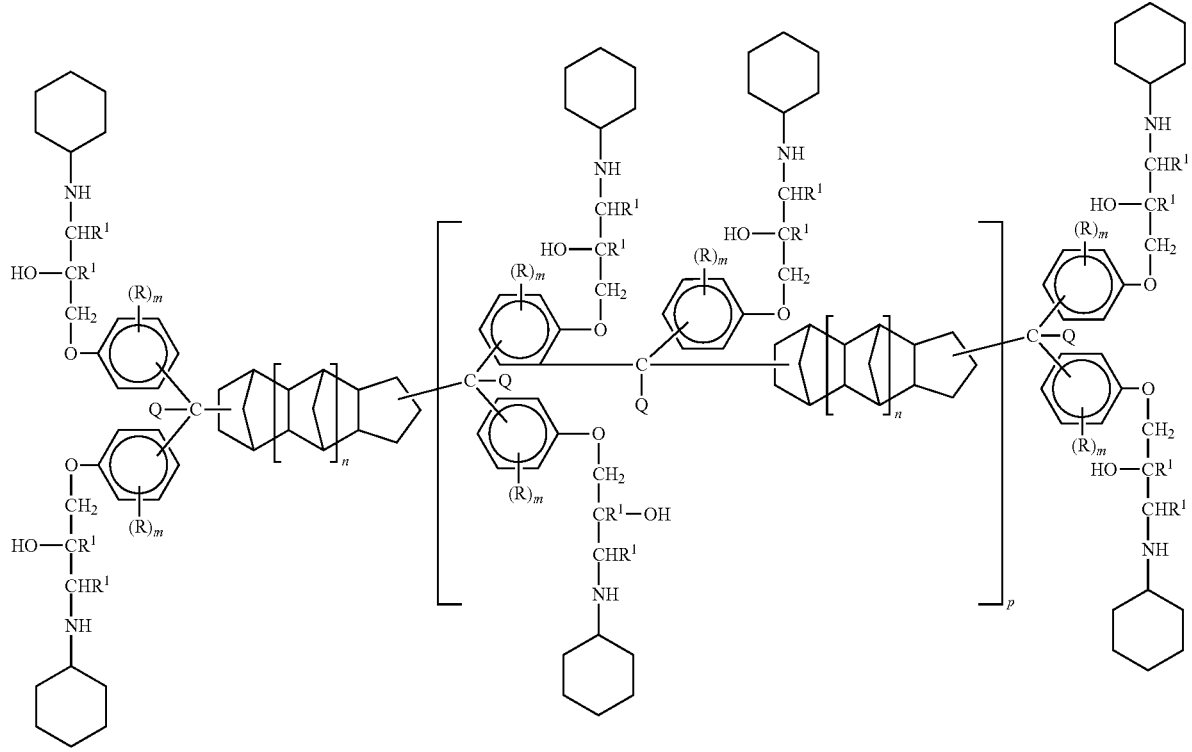

The hydrogen containing compound may be selected from the compounds having dual functional groups, such as (f) sulfonamides, (g) aminophenols, (h) aminocarboxylic acids, (i) phenolic hydroxyl containing carboxylic acids, and (j) sulfanilamides. These compounds may be utilized to provide an adduct with different functional groups of different reactivity for curing an epoxy resin. An example of this type of adduct is a reaction product of an aminophenol compound, p-N-methylaminomethylphenol (as the hydrogen containing compound), with a polycyclopentadiene compound of Formula I and/or Formula III. The reaction provides the adduct with phenolic hydroxyl terminated groups when the reaction is under mild conditions including (a) with no catalyst, (b) at low temperature (e.g. about 25° C. to about 50° C.), (c) for a relatively long reaction time, (d) using incremental or slow continuous addition of the polyglycidyl ether to a large stoichiometric excess of the hydrogen containing compound, and (e) both the polyglycidyl ether (A) and the hydrogen containing compound are in solvent. The following idealized adduct structure of Formula XI prepared using the epoxy resin of Formula I shows the adduct comprising phenolic hydroxyl terminated groups:

A catalyzed reaction favoring one functional group over another with the epoxide group may also be employed. For example, when a hydrogen containing compound comprising at least two different functional groups each bearing at least one reactive hydrogen atom is used to form the adduct of the present disclosure, a catalyst which favors a reaction of reactive hydrogen atom(s) of one type of functional group with an epoxide group over a reaction of reactive hydrogen atom(s) of the other type of functional group with an epoxide group may be employed.

The adduct may also include at least one oligomeric component derived from a reaction of epoxide groups from at least two separate polycyclopentadiene compounds of the present disclosure with each respective polycyclopentadiene compound having one of the epoxide groups already reacted with the reactive hydrogen atoms in the hydrogen containing compound.

An example of this type of adduct structure is a reaction product of a polyglycidyl ether of Formula I and cyclohexylamine as illustrated by the compound of Formula XII. The following idealized adduct structure of Formula XII shows that the oligomeric component is derived from at least two Formula XI:

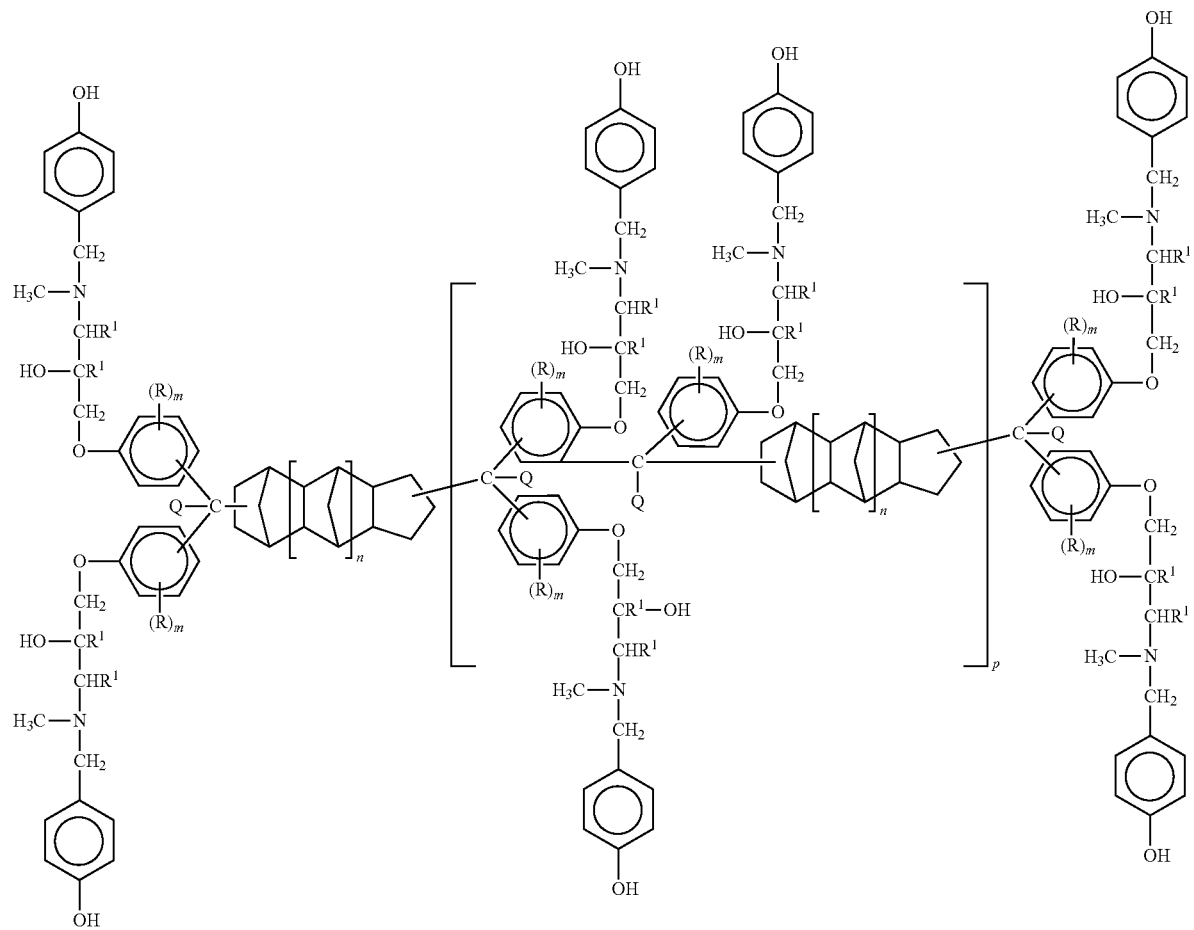

epoxide groups from two separate polyglycidyl ethers each with one of the epoxide groups already reacted with cyclohexylamine:

epoxy resin and a hydroxyl group of a 2-hydroxypropyl linkage from an adduct of the present disclosure; or (2) a reaction between three separate polycyclopentadiene compounds of Formula XII:

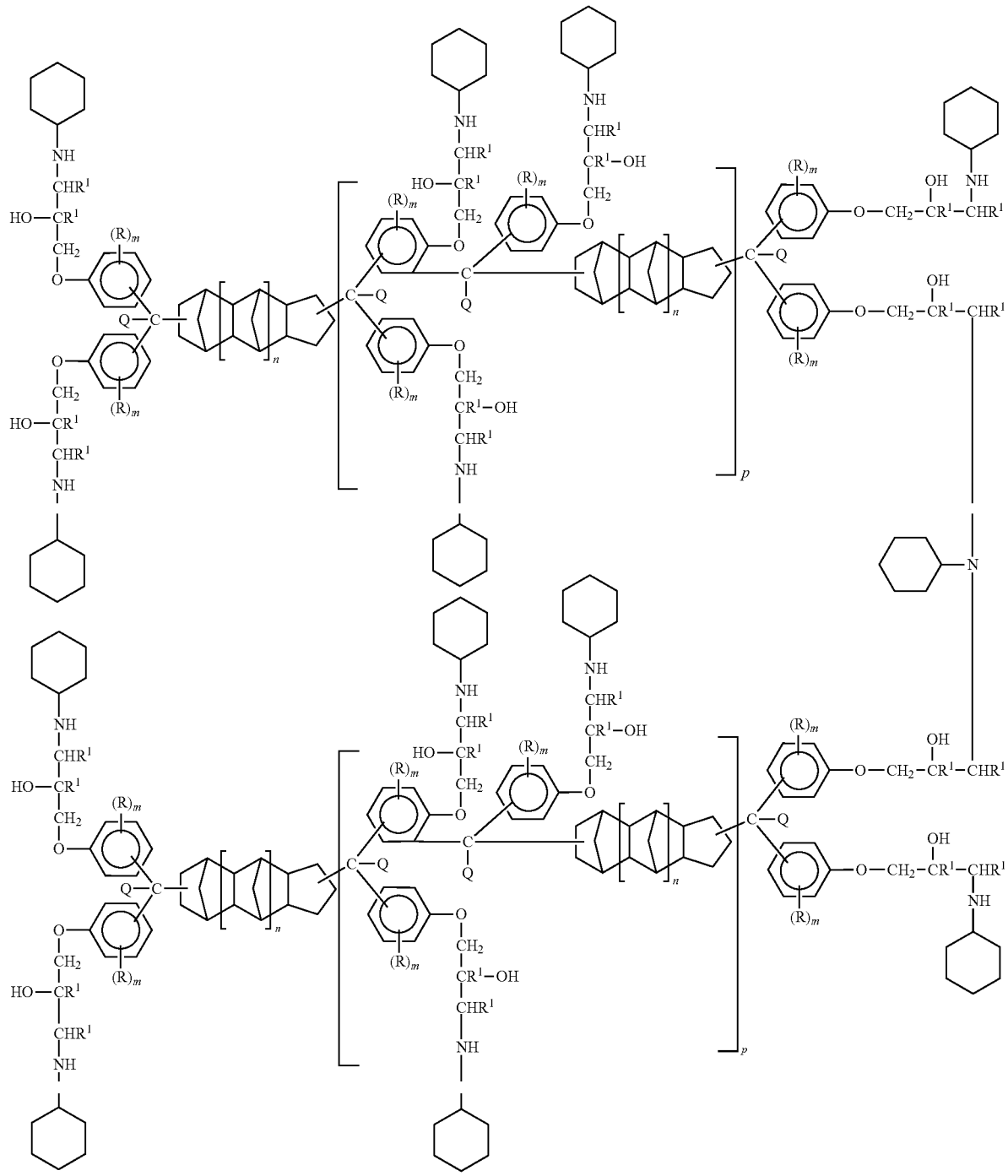

The adduct may also include at least one branched or crosslinked adduct structure derived from one of the following reactions: (1) a reaction between an epoxide group from an polycyclopentadiene compound of the present disclosure that has already been adducted at another epoxide group of an epoxy resin and a hydroxyl group of a 2-hydroxypropyl linkage from an adduct of the present disclosure; or (2) a reaction between three separate polycyclopentadiene compounds of the present disclosure with three reactive hydrogen atoms from the hydrogen containing compound of the present disclosure.

An example of the above reaction (1) is a reaction of a hydroxyl group from an adduct of the polyglycidyl ether of the polycyclopentadiene compounds of Formula I and cyclohexylamine with an epoxide group from a second polycyclopentadiene compound of Formula I that has already been adducted with cyclohexylamine at one of the epoxide groups. The chemical structure of the resultant reaction product is shown as a compound of Formula XIII as follows:

An example of the above reaction (2) is a reaction of an amino hydrogen of the adduct of diethylenetriamine and the polycyclopentadiene compound of Formula I where an epoxide group from a second of the polycyclopentadiene compound of Formula I that has already reacted with another amino hydrogen in the diethylenetriamine moiety. The partial Formula XIII:

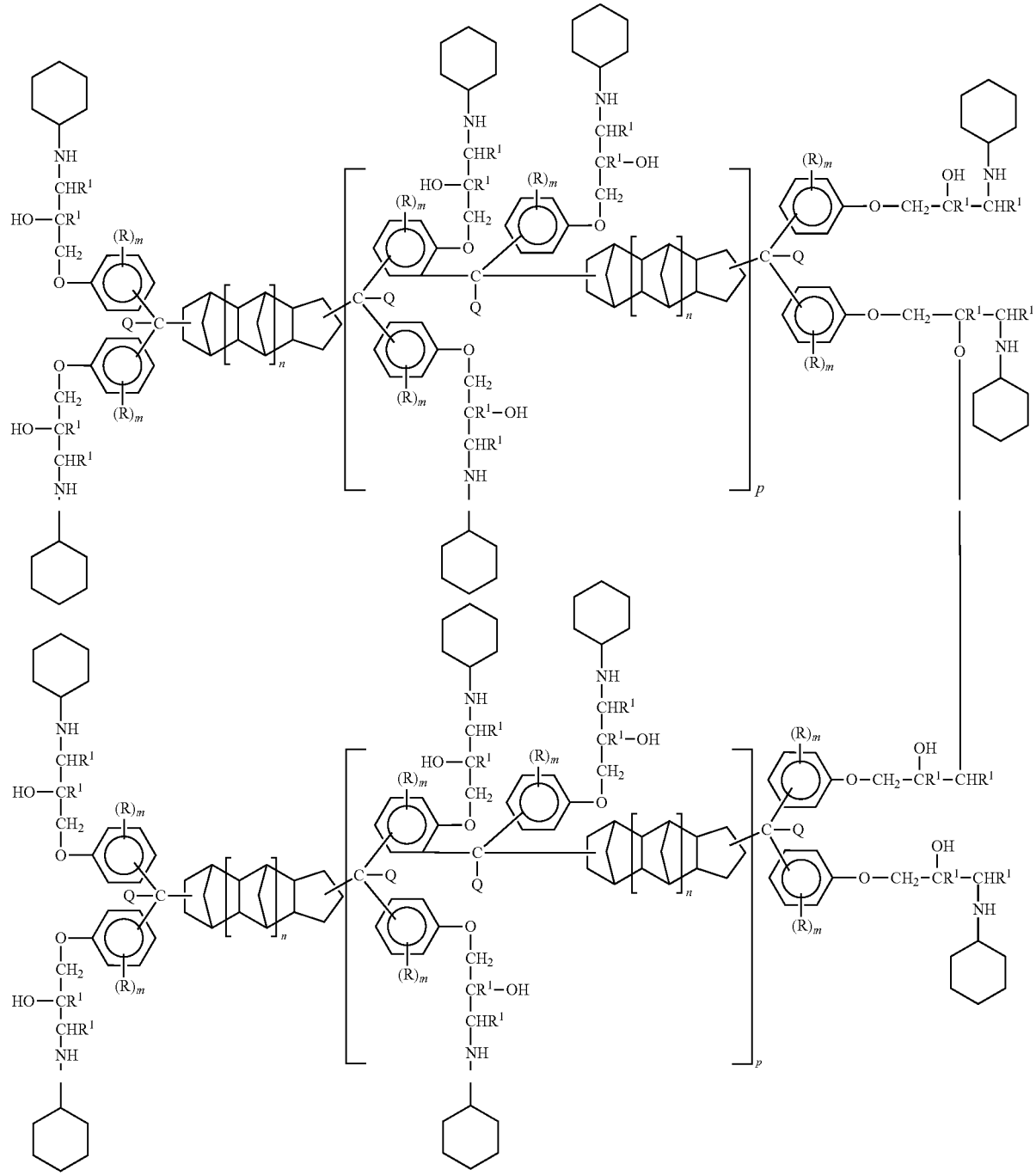

chemical structure of the resultant reaction product is shown as a structure of Formula XIV as follows (only the immediate structure from reaction of the glycidyl ether groups and diethylenetriamine is shown):

Formula XIV:

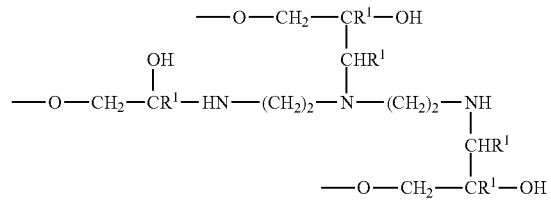

In addition, some minor structures may be present in the adduct of the present disclosure, for example, 1,2-glycol groups derived from a hydrolysis of an epoxide group in the epoxy resin, or halomethyl groups derived from an addition of epihalohydrin to a hydroxyl group of an intermediate halohydrin molecule during the process of forming the epoxy resin.

Other minor structures may be formed via a reaction of a backbone hydroxyl group in the adduct of the polycyclopentadiene compounds of Formula I. For example, a reaction of the secondary hydroxyl group with a carboxylic acid group present in certain of the hydrogen containing compounds, results in the formation of a backbone ester linkage in the adduct.

Curable Compositions

For the various embodiments, the curable compositions of the present disclosure can include (a) an adduct of the present disclosure and (b) an epoxy resin material comprising one or more resin compound(s), one or more polycyclopentadiene compounds of Formula I and/or Formula III, or mixtures thereof. As discussed herein, the adduct of the present disclosure includes (1) at least one reaction product of the polycyclopentadiene compounds of Formula I and/or Formula III, (2) the hydrogen containing compound, and optionally, (3) the resin compound.

For the various embodiments, the curable composition of the present disclosure can be prepared by mixing the adduct of the present disclosure with the epoxy resin material in amounts which will effectively cure the curable composition, with the understanding that the amounts will depend upon the specific adduct and the resin compound employed.

For the various embodiments, the epoxy resin that can be used as the epoxy resin material for the curable composition of the present disclosure may be an epoxide-containing compound which has an average of more than one epoxide group per molecule. Examples of the epoxy resin include those epoxy resins which are suitable for the resin compound, as well as the polycyclopentadiene compounds of Formula I and/or Formula III, as described herein.

Generally, the ratio of the adduct of the present disclosure and the epoxy resin material is from about 0.60:1 to about 1.50:1, and preferably from about 0.95:1 to about 1.05:1 equivalents of reactive hydrogen atom present in the adduct per equivalent of epoxide group in the epoxy resin material at the conditions employed for curing.

Preferred curable compositions of the present disclosure includes (1) the adduct of the present disclosure and (2) the epoxy resin material, where the epoxy resin material includes one or more of epoxy resins, which include those epoxy resins that are suitable for the epoxy resin of Formula I and/or Formula III described herein, and the adduct includes at least one reaction product of the polycyclopentadiene compounds of Formula I and/or Formula III and the hydrogen containing compound, as discussed herein. The hydrogen containing compound, for example, includes an aliphatic or cycloaliphatic diamine, an aliphatic or cycloaliphatic polyamine, an aliphatic or cycloaliphatic dicarboxylic acid, or an aliphatic or cycloaliphatic aminocarboxylic acid, a diaminocarboxylic acid, an aminodicarboxylic acid, or a diaminodicarboxylic acid and combinations thereof.

Process Conditions for Curing the Curable Composition For the various embodiments, the process of curing the curable composition of the present disclosure may be conducted at atmospheric (e.g. 760 mm Hg), superatmospheric or subatmospheric pressures and at a temperature from about 0° C. to about 300° C., preferably from about 25° C. to about 250° C., and more preferably from about 50° C. to about 200° C.

The time required to complete the curing may depend upon the temperature employed. Higher temperatures generally require a shorter period of time whereas lower temperatures generally require longer periods of time. In general, the required time for completion of the curing is from about 1 minute to about 48 hours, preferably from about 15 minutes to about 24 hours, and more preferably from about 30 minutes to about 12 hours.

It is also operable to partially cure the curable composition of the present disclosure to form a B-stage product and subsequently cure the B-stage product completely at a later time. The curable composition of the present disclosure may also include a curing agent and/or a curing catalyst.

Examples of the curing agent and/or catalyst useful for the curable composition include aliphatic, cycloaliphatic, polycycloaliphatic or aromatic primary monoamines, aliphatic, cycloaliphatic, polycycloaliphatic or aromatic primary and secondary polyamines, carboxylic acids and anhydrides thereof, aromatic hydroxyl containing compounds, imidazoles, guanidines, urea-aldehyde resins, melamine-aldehyde resins, alkoxylated urea-aldehyde resins, alkoxylated melamine-aldehyde resins, amidoamines, epoxy resin adducts, and combinations thereof.

Particularly preferred examples of the curing agent include methylenedianiline; 4,4'-diaminostilbene; 4,4'-diamino-alpha-methylstilbene; 4,4'-diaminobenzanilide; dicyandiamide; ethylenediamine; diethylenetriamine; triethylenetetramine; tetraethylenepentamine; urea-formaldehyde resins; melamine-formaldehyde resins; methylolated urea-formaldehyde resins; methylolated melamine-formaldehyde resins; bisphenols such as bisphenol A; bisphenol F (bis-4-hydroxyphenyl methane); bisphenol S (bis-4-hydroxyphenyl sulfone); TBBA (tetrabromobisphenol A); phenol-formaldehyde novolac resins; cresol-formaldehyde novolac resins; sulfanilamide; diaminodiphenylsulfone; diethyltoluenediamine; t-butyltoluenediamine; bis-4-aminocyclohexylamine; isophoronediamine; diaminocyclohexane; hexamethylenediamine, piperazine; 1-(2-aminoethyl)piperazine; 2,5-dimethyl-2,5-hexanediamine; 1,12-dodecanediamine; tris-3-aminopropylamine; and combinations thereof.

Particularly preferred examples of the curing catalyst include boron trifluoride, boron trifluoride etherate, aluminum chloride, ferric chloride, zinc chloride, silicon tetrachloride, stannic chloride, titanium tetrachloride, antimony trichloride, boron trifluoride monoethanolamine complex, boron trifluoride triethanolamine complex, boron trifluoride piperidine complex, pyridine-borane complex, diethanolamine borate, zinc fluoroborate, metallic acylates such as stannous octoate or zinc octoate and combinations thereof.

For the various embodiments, the curing catalyst may be employed in an amount that will effectively cure the curable composition. The amount of the curing catalyst may also depend upon the particular adduct, epoxy resin, and curing agent, if any, employed in the curable composition.

Generally, the curing catalyst may be used in an amount of from about 0.001 to about 2 percent by weight of the total curable composition. In addition, one or more of the curing catalysts may be employed to accelerate or otherwise modify the curing process of the curable composition.

The curing agent may be employed in conjunction with the adduct to cure the curable composition. The amounts of combined curing agent and adduct are from about 0.60:1 to about 1.50:1, and preferably from about 0.95:1 to about 1.05:1 equivalents of reactive hydrogen atom collectively in the curing agent and the adduct.

For the various embodiments, the curable composition may also be blended with at least one additive including, for example, a cure accelerator, a solvent or diluent, a modifier such as a flow modifier and/or a thickener, a reinforcing agent, a filler, a pigment, a dye, a mold release agent, a wetting agent, a stabilizer, a fire retardant agent, a surfactant and combinations thereof.

For the various embodiments, the additive may be blended with the adduct or with the resin compound or with both the adduct and the resin compound prior to use for the preparation of the curable composition of the present disclosure. The additives may be added in functionally equivalent amounts, for example, the pigment and/or dye may be added in quantities that will provide the composition with the desired color. In general, the amount of the additives may be from about zero to about 20 percent, preferably from about 0.5 to about 5 percent, and more preferably from about 0.5 to about 3 percent by weight based upon the total weight of the curable composition.

For the various embodiments, the cure accelerator that can be employed herein includes, for example, mono, di, tri and tetraphenols; chlorinated phenols; aliphatic or cycloaliphatic mono or dicarboxylic acids; aromatic carboxylic acids; hydroxybenzoic acids; halogenated salicylic acids; boric acid; aromatic sulfonic acids; imidazoles; tertiary amines; aminoalcohols; aminopyridines; aminophenols; mercaptophenols and combinations thereof.

Particularly suitable cure accelerators include 2,4-dimethylphenol; 2,6-dimethylphenol; 4-methylphenol; 4-tertiary-butylphenol; 2-chlorophenol; 4-chlorophenol; 2,4-dichlorophenol; 4-nitrophenol; 1,2-dihydroxybenzene; 1,3-dihydroxybenzene; 2,2'-dihydroxybiphenyl; 4,4'-isopropylidenediphenol; valeric acid; oxalic acid; benzoic acid; 2,4-dichlorobenzoic acid; 5-chlorosalicylic acid; salicylic acid; p-toluenesulfonic acid; benzenesulfonic acid; hydroxybenzoic acid; 4-ethyl-2-methylimidazole; 1-methylimidazole; triethylamine; tributylamine; N,N-diethylethanolamine; N,N-dimethylbenzylamine; 2,4,6-tris(dimethylamino)phenol; 4-dimethylaminopyridine; 4-aminophenol; 2-aminophenol; 4-mercaptophenol and combinations thereof.

Examples of the solvent or diluent which can be employed herein include, for example, aliphatic and aromatic hydrocarbons, halogenated aliphatic hydrocarbons, aliphatic ethers, aliphatic nitriles, cyclic ethers, glycol ethers, esters, ketones, amides, sulfoxides and combinations thereof.

Particularly suitable solvents include pentane, hexane, octane, toluene, xylene, methylethylketone, methylisobutylketone, N,N-dimethylformamide, dimethylsulfoxide, diethyl ether, tetrahydrofuran; 1,4-dioxane, dichloromethane, chloroform, ethylene dichloride, methyl chloroform, ethylene glycol dimethyl ether, diethylene glycol methyl ether, dipropylene glycol methyl ether, N-methylpyrrolidinone; N,N-dimethylacetamide, acetonitrile, sulfolane, and combinations thereof.

For the various embodiments, the modifier such as the thickener and the flow modifier may be employed in amounts of from zero to about 10, preferably, from about 0.5 to about 6, and more preferably from about 0.5 to about 4 percent by weight based upon the total weight of the curable composition.

The reinforcing material that may be employed herein includes natural and synthetic fibers in the form of woven fabric, mat, monofilament, multifilament, unidirectional fiber, roving, random fiber or filament, inorganic filler or whisker, or hollow sphere. Other suitable reinforcing material includes glass, carbon, ceramics, nylon, rayon, cotton, aramid, graphite, polyalkylene terephthalates, polyethylene, polypropylene, polyesters, and combinations thereof.

For the various embodiments, the filler which may be employed herein includes, for example, inorganic oxide, ceramic microsphere, plastic microsphere, glass microsphere, inorganic whisker, calcium carbonate and combinations thereof. The filler may be employed in an amount of from about zero to about 95, preferably from about 10 to about 80 percent, and more preferably from about 40 to about 60 percent by weight based upon the total weight of the curable composition.

The adduct may also be employed in, for example, coatings, especially protective coatings with excellent solvent resistant, moisture resistant, abrasion resistant, and weatherable properties. Other applications of the adduct of the present disclosure may include, for example, preparation of electrical or structural laminate or composite, filament windings, moldings, castings, encapsulation, and the like.

The following examples are illustrative of the present disclosure, but are not to be construed as to limiting the scope thereof in any manner.

EXAMPLES

Unless otherwise indicated, all parts and percentages are by weight. Unless otherwise specified, all instruments and chemicals used are commercially available.

Materials $Rh(CO)_2$(acetylacetonate) ($Rh(CO)_2$acac) available from Strem Chemicals Inc.

n-butyldiphenylphosphine available from Organometallics, Inc (E. Hampstead, N.H., USA).

Dicyclopentadiene available from The Dow Chemical Co.

Syngas available from Airgas Great Lakes, Inc.

KBr plate available from Sigma-Aldrich.

90% purity 3-Mercaptopropane-1-sulfonic acid, sodium salt available from Sigma-Aldrich.

Hydrochloric acid available from Sigma-Aldrich.

Phenol available from Sigma-Aldrich.

Tetrahydrofuran available from Sigma-Aldrich.

Methanol available from Sigma-Aldrich.

Anhydrous acetone available from Sigma-Aldrich.

Dichloromethane available from Sigma-Aldrich.

Reference Example 1

Preparation of Dicyclopentadiene Polyphenol

A. Preparation of Dicyclopentadiene Dialdehyde

A reaction mixture of $Rh(CO)_2$acac (35.1 mg; 0.136 mmol) and n-butyldiphenylphosphine (0.33 g; 1.36 mmol)

(molar ratio L/Rh=10) in dicyclopentadiene (70 g) was prepared in a purge box under dry nitrogen, and then placed in a 150 mL Parr reactor and sparged three times with 1:1 syngas (1:1 molar ratio CO:$H_2$) at 20° C. The reaction mixture was then heated to 100° C. at a pressure of 90 psi of syngas with stirring. The product formation from the reaction mixture was monitored by Gas Chromatography (GC) [Agilent 6890], where the final GC analysis of the resulting mixture showed the dicyclopentadiene dialdehyde (87 area % in GC at 10.4-10.7 minutes (min)) and the dicyclopentadiene monoaldehyde (6 area % in GC at 5.6 and 6.0 min). The dicyclopentadiene reactant was completely consumed. Very minor signals of higher molecular weight byproducts at higher retention times (21-22.5 min) were also observed. Gas chromatographic/mass spectroscopic (GC/MS) analysis [Agilent 6890 GC with Agilent 5973 Mass Selective Detector] of the reaction mixture supported the formation of the desired dicyclopentadiene dialdehyde ($M^+$=192) and saturated dicyclopentadiene monoaldehyde ($M^+$=164).

$^1$H NMR (δ, $CDCl_3$, ppm): 1.2-2.8 m (17H, CH+$CH_2$), 9.28-9.57 m (2H, CHO). $^{13}$C NMR (δ, $CDCl_3$, ppm): 23.66; 23.81; 24.35; 25.90; 25.97; 27.82; 27.97; 29.45; 29.63; 40.65; 40.92; 41.03; 41.38; 45.42; 45.50; 45.58; 45.64; 45.70; 46.07; 46.11; 48.36; 48.65; 49.17; 53.17; 53.21; 54.57; 202.86; 202.89; 202.92; 202.95; 203.03; 203.07; 203.09; 203.14.

Fourier transform infrared spectrophotometric (FTIR, Nicolet Avatar 3700 DTGS FTIR (Thermo Electron Corporation)) analysis of a neat film of the dicyclopentadiene dialdehyde on a KBr plate revealed the expected strong aldehyde carbonyl stretch at 1720.4 $cm^{-1}$. The product was obtained as a brown liquid in the amount of 97.7 g.

B. Preparation of 3-Mercapto-1-Propane Sulfonic Acid Catalyst

3-Mercaptopropane-1-sulfonic acid, sodium salt was added to concentrated hydrochloric acid (35.7% aqueous, 200 mL) which was magnetically stirred in a glass beaker. After covering with a sheet of Parafilm "M" (American National Can, Greenwich, Conn.) to prevent uptake of atmospheric moisture, the resulting white crystalline slurry was stirred for 5 minutes then filtered over a medium fritted glass funnel. The filtrate was rotary evaporated to give 8.88 g of a pale yellow tacky solid product which was used as the catalyst without further processing.

C. Phenolation Reaction

Dicyclopentadiene dialdehyde (48.06 g, 0.25 mole uncorrected) from section A (above) and molten phenol (470.5 g, 5.0 moles) were added to a 1 L glass three neck round bottom reactor. The reactor was additionally outfitted with an ambient temperature (22° C.) condenser and a thermometer, both affixed to the reactor via a Claisen adaptor, plus an overhead nitrogen inlet, a glass stirring shaft with a Teflon™ (E.I. du Pont de Nemours) stirrer blade which was coupled to a variable speed motor to provide mechanical stirring and a thermostatically controlled heating mantle.

Overhead nitrogen flow (0.5 L per minute) commenced, followed by heating, then stirring. Twenty minutes later, the temperature reached 65° C., forming a clear light yellow colored solution. At this time, addition of aliquots of the 3-mercapto-1-propane sulfonic acid (total catalyst used was 1.95 g, 0.05 mole % with respect to dicyclopentadiene dialdehyde reactant) commenced into the stirred solution. The initial aliquot of catalyst (0.39 g) induced a maximum exotherm to 70° C. after 3 minutes, turning the solution dark amber. The heating mantle was removed from the reactor, and a fan was engaged to cool the reactor exterior back to 65° C. A second aliquot of the 3-mercapto-1-propane sulfonic acid (0.22 g) was added, with continuation of the cooling. The second aliquot of the catalyst induced an exotherm to 66° C. one minute after addition, with cooling back to 65° C. after an additional 2 minutes. At this time, a third aliquot of the 3-mercapto-1-propane sulfonic acid (0.35 g) was added inducing an exotherm to 68° C. 2 minutes later. After an additional 3 minutes the temperature had cooled back to 65° C. and the cooling fan was shut off. A fourth aliquot of the 3-mercapto-1-propane sulfonic acid (0.24 g) was added with maintenance of the 65° C. reaction temperature. After 5 minutes, a fifth aliquot of the 3-mercapto-1-propane sulfonic acid (0.37 g) was added with maintenance of the 65° C. reaction temperature followed by a decline to 62.5° C. over the next 5 minutes. At this time, cooling of the reactor exterior ceased, the heating mantle was replaced on the reactor, and the final aliquot of the 3-mercapto-1-propane sulfonic acid (0.38 g) was added to the dark amber colored solution.

The reaction temperature was maintained at 65° C. to 66° C. for the next 22.25 hours during which time, the course of the reaction was followed via HPLC analysis [Hewlett Packard 1090 Liquid Chromatograph using a Zorbax Eclipse® (Agilent) XDB-C8 analytical column (5μ, 4.6×150 mm) with an Eclipse® (Agilent) XDB-C8 analytical guard column (5μ, 4.6×12.5 mm)]. The columns were maintained in the chromatograph oven at 40° C. Acetonitrile and water (treated with 0.05% aqueous o-phosphoric acid) were used as the eluents and were initially delivered via the pump at a rate of 1.000 mL per minute as a 70/30% solution, respectively, changing after 5 minutes to a 90/10% solution and held therein for the next 15 minutes. The acetonitrile used was HPLC grade, 100.0% purity (by gas chromatography), with a UV cutoff of 189 nm. The o-phosphoric acid used was nominally 85% pure (actual assay 85.1%). The water used was HPLC grade. A diode array detector employed for the sample analysis was set at 225 nm and the reference was set at 550 nm. After 1.6 hours of reaction, HPLC analysis revealed full conversion of the dicyclopentadiene dialdehyde to a distribution of products, with little change in the product thereafter.

At the end of the reaction time, the reactor contents were equally divided into a pair of beakers, each containing 3 L of magnetically stirred deionized (DI) water. Stirring ceased after 75 minutes and the contents of the beakers were allowed to settle overnight. The following day, each beaker was decanted to a volume of 500 mL with the decanted aqueous product disposed as waste. Both beakers were refilled with fresh DI water to 3.5 L total volume, stirring and heating commenced until 50° C. was achieved causing viscous strings of reddish amber colored product to form in the bottom of each beaker. Stirring and heating ceased and the contents of the beakers were allowed to settle overnight. The following day, each beaker was decanted to remove the aqueous product for disposal as waste. Boiling DI water (1.5 L) was added to the dark yellow orange colored product remaining in each beaker and magnetic stirring resumed with heating to a boil. Once boiling was achieved, heating ceased and stirring continued as the product slurry cooled to 20° C. Once a temperature of 20° C. was reached, the solids were collected by decantation through filter paper. The solids were added to a ceramic dish and dried in the vacuum oven at 100° C. for 16 hours, removed, ground to a fine powder and dried in the vacuum oven for an additional 6.5 hours to provide 119.79 g of the dicyclopentadiene polyphenol as a mustard yellow colored powder.

FTIR spectrophotometric analysis of a KBr pellet revealed complete disappearance of the aldehyde carbonyl stretch at 1720.4 $cm^{-1}$ with appearance of strong aromatic ring absorbance at 1610.9 $cm^{-1}$ (shoulder at 1595.7 $cm^{-1}$) and 1510.0 $cm^{-1}$, broad strong hydroxyl O—H stretching centered at 3382.2 cm$^{-1}$, and broad strong C—O stretching at 1226.7 (shoulder at 1170.7) cm$^{-1}$. HPLC analysis revealed the resulting dicyclopentadiene polyphenol included 12 components with 6 predominant components comprising 27.9, 4.2, 6.8, 11.0, 21.6 and 22.2 area %.

Example 1

Conversion of Dicyclopentadiene Polyphenol to the Polyglycidyl Ether

A one liter, three neck glass round bottom reactor was charged with the dicyclopentadiene polyphenol (53.27 grams, 0.40 hydroxyl equivalent, based on 133.2 nominal hydroxyl equivalent weight) prepared as discussed above and epichlorohydrin (277.7 grams, 3.0 moles). The reactor was additionally equipped with a condenser (maintained at 0° C.), a thermometer, a Claisen adaptor, an overhead nitrogen inlet (1 liter per minute), and a stirred assembly (Teflon™ (E.I. du Pont de Nemours) paddle, glass shaft, variable speed motor). Sodium hydroxide (14.4 grams, 0.36 mole) was dissolved in deionized water (57.6 grams) to form an aqueous sodium hydroxide solution. The aqueous sodium hydroxide solution was added to a side arm vented addition funnel and then attached to the reactor.

Stirring of the slurry commenced with heating using a thermostatically controlled heating mantle. Once the stirred slurry was at 30° C., isopropanol (149.5 grams, 35% weight of the epichlorohydrin used) was added with continued stirring and heating. Once 38° C. was achieved, a solution formed and deionized water (24.2 grams, 8% weight of the epichlorohydrin used) was added by rapid dropwise addition. Once 50° C. was achieved, dropwise addition of the aqueous sodium hydroxide solution from the side arm vented addition funnel commenced causing the solution to initially turn an amber red color. Continued dropwise addition of the aqueous sodium hydroxide at 50° C. slightly clouded the amber red solution. The addition was completed over 50 minutes. After 25 minutes of post reaction, stirring ceased and the reactor contents were allowed to settle. The progress of the epoxidation reaction was monitored by high pressure liquid chromatographic (HPLC) analysis.

At the end of the settling time, the reactor contents were added to a separatory funnel. The aqueous layer was removed, discarded as waste and the organic layer recovered and added back into the reactor. Heating and stirring resumed re-established the 50° C. temperature. Dropwise addition of a second portion of the sodium hydroxide (6.4 grams, 0.16 moles) dissolved in deionized water (25.6 grams) commenced and was completed over 20 minutes while maintaining the temperature at 50° C. After 25 minutes of postreaction, stirring ceased, the reactor contents allowed to settle for 5 minutes in a separatory funnel, the aqueous layer removed from the product, the slightly cloudy light orange colored organic layer added back into the reactor, a sample was removed for HPLC analysis, heating and stirring resumed reestablishing the 50° C. temperature. A third portion of sodium hydroxide (2.0 grams, 0.05 moles) dissolved in deionized water (8.0 grams), respectively, was added over 10 minutes and processed using the method employed for the second aqueous sodium hydroxide addition. After 25 minutes of postreaction followed by removal of the aqueous layer from the final aqueous sodium hydroxide addition, the organic layer was diluted with methylisobutylketone (1 liter) and washed with a second portion (300 milliliters) of deionized water. The aqueous layer was resolved from the product via centrifuging. Third and fourth washes with deionized water (300 milliliters per wash) were completed using the method employed for the first wash (no centrifuging was necessary to resolve the aqueous and organic layers). The recovered organic solution was vacuum filtered over a bed of diatomaceous earth packed in a medium fitted glass funnel with methylisobutylketone used as needed to wash product from the filter bed into the filtrate. Rotary evaporation of the organic layer using a maximum oil bath temperature of 75° C. removed the bulk of the volatiles. Further rotary evaporation at 150° C. to a final vacuum of 0.23 mm of Hg gave 49.02 grams of slightly hazy, light yellow amber colored solid upon cooling to 23° C.

Gas chromatographic (GC) analysis [Hewlett Packard 5890 Series II Gas Chromatograph using a 60 m×0.248 mm×J&W GC column with DB-1 stationary phase, flame ionization detector operating at 300° C., a 300° C. injector temperature, helium carrier gas flow through the column was maintained at 1.1 mL per min, and an initial 50° C. oven temperature with heating at 12° C. per minute to a final temperature of 300° C.] revealed that essentially all light boiling components, including residual epichlorohydrin, had been removed. HPLC analysis revealed complete conversion of the dicyclopentadiene polyphenol to the polyglycidyl ether. Titration of a pair of aliquots of the product demonstrated as average of 20.39% epoxide (211.06 epoxide equivalent weight). Titration of epoxy resins is described by Jay, R. R., "Direct Titration of Epoxy Compounds and Aziridines", Analytical Chemistry, 36, 3, 667-668 (March, 1964). Briefly, in our adaptation of this method, the weighed sample (sample weight ranges from 0.1-0.2 g using a scale with 3 decimal place accuracy) was dissolved in dichloromethane (15 mL) followed by the addition of tetraethylammonium bromide solution in acetic acid (15 mL). The resultant solution treated with 3 drops of crystal violet solution (0.1% w/v in acetic acid) was titrated with 0.1N perchloric acid in acetic acid on a Metrohm 665 Dosimat titrator (Brinkmann). Titration of a blank consisting of dichloromethane (15 mL) and tetraethylammonium bromide solution in acetic acid (15 mL) provided correction for solvent background.

Example 2

Thermally Induced Curing of Polyglycidyl Ether of Dicyclopentadiene Polyphenol with 4,4'-Diaminodiphenyl Methane Polyglycidyl ether of dicyclopentadiene polyphenol (0.5755 gram, 0.002727 epoxide equivalent) from Example 1 and 4,4'-diaminodiphenyl methane (0.1352 gram, 0.002727 —NH equivalent) were weighed into a glass vial and thoroughly ground together to a homogeneous fine powder. Differential scanning calorimetry (DSC) analysis of portions (8.30 and 8.50 milligrams) of the blend was completed using a rate of heating of 7° C. per minute from 25° C. to 425° C. under a stream of nitrogen flowing at 35 cubic centimeters per minute. An exotherm attributed to reaction of epoxide groups with the primary amine hydrogen was observed with an average 84.1° C. onset, a 145.7° C. maximum and a 225.7° C. endpoint accompanied by an average enthalpy of 205.0 joules per gram. A second exotherm attributed to reaction of epoxide groups with the resultant secondary amine hydrogen was observed with an average 247.9° C. onset, a 368.6° C. maximum and a 409.7° C. endpoint accompanied by an average enthalpy of 200.8 joules per gram.

The remaining curable blend was placed into an oven and maintained at 100° C. for one hour, then removed and immediately placed into a second oven and maintained at 150° C.

for one hour, and finally removed and immediately placed into a third oven and maintained at 200° C. for 2 hours followed by slowly cooling over 30 minutes to room temperature. The thermoset resin was transparent, light green colored solid. DSC analysis of a portion (27.0 milligrams) of the blend was completed using a rate of heating of 10° C. per minute from 25° C. to 300° C. under a stream of nitrogen flowing at 35 cubic centimeters per minute. A glass transition temperature (Tg) of 232.2° C. was obtained with a slight exothermic shift commencing at 274.0° C. A second scanning was completed using the aforementioned conditions, resulting in a Tg of 250.2° C. with no residual exothermicity observed.

Example 3

Thermally Induced Curing of Polyglycidyl Ether of Dicyclopentadiene Polyphenol with Dicyanadiamide Polyglycidyl ether of dicyclopentadiene polyphenol (0.7639 gram, 0.00362 epoxide equivalent from Example 1 and powdered (unaccelerated) dicyandiamide (0.0318 gram, 4% weight of the polyglycidyl ether used) were weighed into a glass vial and thoroughly ground together to a homogeneous fine powder. DSC analysis of a portion (8.60 milligrams) of the blend was completed using a rate of heating of 7° C. per minute from 25° C. to 350° C. under a stream of nitrogen flowing at 35 cubic centimeters per minute. An exotherm attributed to reaction of epoxide groups with the dicyandiamide was observed with 160.5° C. onset, a 197.2° C. maximum and a 247.5° C. endpoint accompanied by an average enthalpy of 232.8 joules per gram.

The remaining curable blend was placed into an oven and maintained at 100° C. for one hour, then removed and immediately placed into a second oven and maintained at 150° C. for one hour, and finally removed and immediately placed into a third oven and maintained at 200° C. for 2 hours followed by slowly cooling over 30 minutes to room temperature. The thermoset resin was hazy, yellow colored solid. DSC analysis of a portions (21.4 and 24.0 milligrams) of the blend was completed using a rate of heating of 10° C. per minute from 25° C. to 300° C. under a stream of nitrogen flowing at 35 cubic centimeters per minute. An average substantial exothermic shift was observed commencing at 229.8° C. A second scanning was completed using the aforementioned conditions, resulting in a Tg of 214.8° C. with residual exothermicity observed commencing at 267.6° C. A third scanning was completed using the aforementioned conditions, resulting in a Tg of 219.8 with residual exothermicity observed commencing at 279.4° C.

Example 4

Synthesis of the Ethylenediamine Adduct of the Polyglycidyl Ether of Dicyclopentadiene Polyphenol A. Characterization of Polyglycidyl Ether of Dicyclopentadiene Polyphenol A polyglycidyl ether of dicyclopentadiene polyphenol was prepared using the method of Example 1. Titration of an aliquot of the epoxy resin demonstrated 20.88% epoxide (206.085 epoxide equivalent weight).

B. Adduct Synthesis

A 1 liter, three neck, glass, round bottom reactor with magnetic stirring bar was charged with ethylenediamine (300.4 grams, 20.0 —NH equivalent). The reactor was additionally equipped with a condenser, a nitrogen inlet with 1 liter per minute nitrogen flow and a thermometer. Stirring of the solution under a nitrogen atmosphere commence with heating using a thermostatically controlled heating mantle place under the reactor. Once the stirred solution reached 50° C., dropwise addition of polyglycidyl ether of a dicyclopentadiene polyphenol (4.12 grams, 0.020 epoxide equivalent) from section A above dissolved in anhydrous tetrahydrofuran (50 milliliters) commenced and was completed over the next 6 hours while maintaining the 50° C. reaction temperature.

The solution was held at 50° C. for the next 15.2 hours. After cooling to room temperature, the recovered solution was rotary evaporated to a final vacuum of 12.8 mm Hg using a maximum oil bath temperature of 100° C. The product was recovered (5.39 grams) as a yellow colored, slightly tacky, solid. Titration of an aliquot of adduct revealed an amine hydrogen equivalent weight of 71.65.

Example 5

Curing of Epoxy Resin of Polyglycidyl Ether of Dicyclopentadiene Polyphenol with Ethylenediamine Adduct of Polyglycidyl Ether of Dicyclopentadiene Polyphenol A. Preparation of Curable (Thermosettable) Blend Polyglycidyl ether of dicyclopentadiene polyphenol (0.3181 gram, 0.001544 epoxide equivalent) from Example 4A and ethylenediamine adduct of polyglycidyl ether of dicyclopentadiene polyphenol (0.1106 gram, 0.001544 —NH equivalent) from Example 4B were weighed using a four place balance into a glass vial. Anhydrous tetrahydrofuran (2 milliliters) and anhydrous methanol (1 milliliter) were then added. The contents of the vial were gently and thoroughly stirred to provide a homogeneous liquid. Devolatilization at room temperature was completed in a vacuum oven to provide a homogeneous, curable, powder product.

B. Curing

Differential scanning calorimetry (DSC) analysis of portions (8.70 and 9.50 milligrams) of the blend were completed using a rate of heating of 7° C. per minute from 20° C. to 426° C. under a stream of nitrogen flowing at 35 cubic centimeters per minute. A pair of broad exotherms was noted during the cure of the formulation:

| Sample (mg) | Onset (° C.) | Maximum (° C.) | End (° C.) | Enthalpy (joules/gram) | Onset (° C.) | Maximum (° C.) | End (° C.) | Enthalpy (joules/gram) |
|---|---|---|---|---|---|---|---|---|
| 8.70 | 58.01 | 94.08 | 161.09 | 21.95 | 197.23 | 334.48 | 413.47 | 347.3 |
| 9.50 | 61.10 | 105.069 | 152.10 | 29.20 | 225.08 | 331.23 | 397.02 | 326.0 |

A second scanning was completed using the aforementioned conditions, resulting in an average Tg of 230.02° C. A third scanning resulted in an average Tg of 221.60° C. A fourth scanning resulted in an average Tg of 225.91° C. There was no evidence of decomposition observed in the repeated DSC analyses. The sample recovered from the DSC analysis was an incompletely fused, transparent, golden colored solid.

Example 6

Curing of Epoxy Resin of Diglycidyl Ether of a 4,4'-Isopropylidenediphenol with Ethylenediamine Adduct of the Polyglycidyl Ether of Dicyclopentadiene Polyphenol A. Preparation of Curable (Thermosettable) Composition Diglycidyl ether of 4,4'-isopropylidenediphenol (0.3533 gram, 0.001955 epoxide equivalent) and ethylenediamine adduct of polyglycidyl ether of dicyclopentadiene polyphenol (0.1401 gram, 0.001955 —NH equivalent) from Example 4B were weighed using a 4 place balance into a glass vial. The diglycidyl ether of 4,4'-isopropylidene diphenol used was D.E.R.™ 383 from The Dow Chemical Company. Anhydrous methanol (2 milliliter) was then added. The contents of the vial were gently and thoroughly stirred to provide a homogeneous liquid. Devolatilization at room temperature was completed in a vacuum oven to provide a homogeneous, curable, liquid product.

B. Curing

Differential scanning calorimetry (DSC) analysis of a portion (10.1 milligrams) of the blend was completed using a rate of heating of 7° C. per minute from 0° C. to 425° C. under a stream of nitrogen flowing at 35 cubic centimeters per minute. A pair of broad exotherms was noted during the cure of the formulation:

| Sample (mg) | Onset (° C.) | Maximum (° C.) | End (° C.) | Enthalpy (joules/gram) | Onset (° C.) | Maximum (° C.) | End (° C.) | Enthalpy (joules/Gram) |
|---|---|---|---|---|---|---|---|---|
| 10.1 | 38.53 | 89.32 | 155.89 | 127.2 | 246.40 | 326.91 | 382.66 | 164.7 |

A second scanning was completed using the aforementioned conditions, resulting in a weak Tg of 267.43° C. There was no evidence of decomposition observed in the DSC analysis. The sample recovered from the DSC analysis was a completely fused, transparent, amber colored solid.

C. Room Temperature Cure

The blend from section A above that had been held at room temperature (20° C.) crosslinked to a transparent, rubbery, light yellow colored solid within 15 minutes after devolatilization. Upon further standing at 20° C., the solid product became rigid.

What is claimed is:

1. A polycyclopentadiene compound of Formula I:

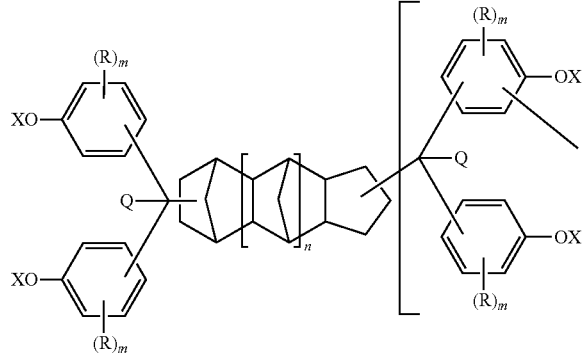

(Formula I)

-continued

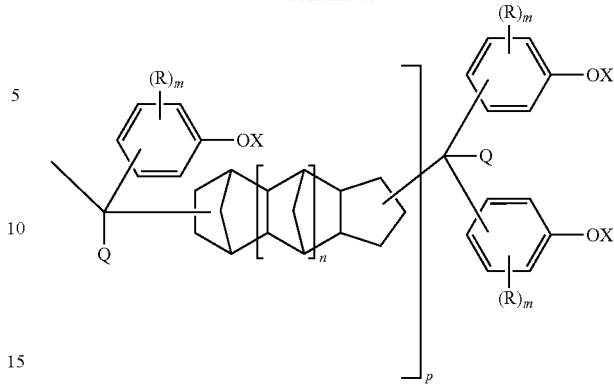

in which X is a structure of Formula II:

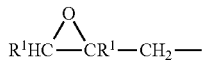

(Formula II)

where each $R^1$ is independently hydrogen or a methyl group, n has an average value from zero to 20; each m independently has a value of zero to 3; each p has a value of zero to 20; each R is independently a halogen, a nitrile group, a nitro group, an alkyl group, an alkoxy group, an alkenyl group, or an alkenyloxy group, where the alkyl group, the alkoxy group, the alkenyl group, and the alkenyloxy group each independently contain 1 to about 6 carbon atoms, and each Q is independently hydrogen or an alkyl group containing 1 to about 6 carbon atoms.

2. The polycyclopentadiene compound of claim 1, where n has an average value from zero to 2.

3. The polycyclopentadiene compound of claim 1, where the alkenyl group is allyl and the alkenyloxy group is allyloxy.

4. The polycyclopentadiene compound of claim 1, where the R group is methyl and m is 1 to 2.

5. The polycyclopentadiene compound of claim 1, where m is zero.

6. The polycyclopentadiene compound of claim 1, where p has a value from zero to 1.

7. An adduct prepared from the polycyclopentadiene compound of claim 1 and a hydrogen containing compound that includes one or more hydrogen atoms reactive with epoxide groups of the polycyclopentadiene compound of Formula II, wherein the hydrogen containing compound is selected from the group consisting of diphenols, polyphenols, dicarboxylic acids, polycarboxylic acids, dimercaptans, polymercaptans, di-amines, polyamines, primary monoamines, sulfonamides, aminophenols, aminocarboxylic acids, phenolic hydroxyl containing carboxylic acids, sulfanilamides, mono-functional phosphorous compounds, and combinations thereof.

8. The adduct of claim 7, where the hydrogen containing compound is selected from the group consisting of a dimercaptan compound, a polymercaptan compound, a diamine compound, a polyamine compound, an amine compound, a primary monoamine compound, a sulfonamide compound, an aminophenol compound, an aminocarboxylic acid compound, a phenolic hydroxyl containing carboxylic acid compound, a sulfanilamide compound, an ammonia compound, a mono-functional phosphorous compound, and combinations thereof.

9. The adduct of claim 7, further prepared from an oligomer of the polycyclopentadiene compound of Formula I and the hydrogen containing compound, where the one or more reactive hydrogen atoms are reactive with epoxide groups of the polycyclopentadiene compound of Formula II.

10. A curable composition, comprising:
a polycyclopentadiene compound of claim 1; and
a hardener.

11. The curable composition of claim 10, where at least a portion of the polycyclopentadiene compound of claim 1 forms an adduct with a hydrogen containing compound that includes one or more reactive hydrogen atoms reactive with epoxide groups of the polycyclopentadiene compound of Formula II.

12. The curable composition of claim 11, including an epoxy compound reactive with at least one of the hardener and the adduct.

13. A curable composition comprising:
an adduct of claim 7; and
a resin.

14. The curable composition of claim 13, where the resin includes a polycyclopentadiene compound as claimed in claim 1.

15. The curable composition of claim 10, further including an oligomer formed from the polycyclopentadiene compound as claimed in claim 1.

16. A cured or partially cured composition resulting from curing the curable composition as claimed in claim 10.

* * * * *